(12) United States Patent
Vanderborght et al.

(10) Patent No.: US 8,133,682 B2
(45) Date of Patent: Mar. 13, 2012

(54) CANCER VACCINE

(75) Inventors: Ann Vanderborght, Hasselt (BE); Monique Ida Jozef Ummelen, Partij Wittem (NL); Franciscus Charles Servatius Ramaekers, Maastricht (NL); Stefan Maarten Van Den Eijnde, 'S Gravenvoeren (BE); Joseph Leonardus Victor Broers, Maastricht (NL); Frank Walter Falkenberg, Dortmund (DE); Christine Hahnel, Dortmund (DE)

(73) Assignee: Mubio Products BV, Maastrict (NL)

(*) Notice: Subject to any disclaimer, the term of this patent is extended or adjusted under 35 U.S.C. 154(b) by 298 days.

(21) Appl. No.: 12/282,532

(22) PCT Filed: Mar. 12, 2007

(86) PCT No.: PCT/EP2007/002140
§ 371 (c)(1),
(2), (4) Date: Nov. 23, 2008

(87) PCT Pub. No.: WO2007/104511
PCT Pub. Date: Sep. 20, 2007

(65) Prior Publication Data
US 2009/0074773 A1  Mar. 19, 2009

(30) Foreign Application Priority Data
Mar. 13, 2006 (EP) .................... 06447035

(51) Int. Cl.
*G01N 33/53* (2006.01)
*G01N 33/574* (2006.01)
*C12Q 1/68* (2006.01)

(52) U.S. Cl. ............................................ 435/7.1; 435/6
(58) Field of Classification Search ........................ None
See application file for complete search history.

(56) References Cited

U.S. PATENT DOCUMENTS

| 7,608,413 B1 * | 10/2009 | Joseloff et al. ............... 435/7.23 |
| 2005/0196754 A1 * | 9/2005 | Drmanac et al. .................. 435/6 |
| 2005/0221342 A1 | 10/2005 | Tang |

FOREIGN PATENT DOCUMENTS

| WO | 01/59063 A | 8/2001 |
| WO | 01/75067 A2 | 10/2001 |
| WO | 03/000928 A | 1/2003 |
| WO | 03/047526 A | 6/2003 |
| WO | 2004/112829 A | 12/2004 |

OTHER PUBLICATIONS

International Search Report dated Aug. 28, 2007 in PCT/EP2007/002140.

* cited by examiner

*Primary Examiner* — Laura B Goddard
(74) *Attorney, Agent, or Firm* — Kristina Castellano; Castellano PLLC

(57) ABSTRACT

The invention relates generally to the field of cancer diagnosis, prognosis, treatment and prevention. More particularly, the present invention relates to methods of diagnosing, treating and preventing lung cancer. In particular, aspects of the invention are directed to methods of diagnosing, treating and preventing small cell lung cancers. Methods of using a nucleic acid and/or a protein, which are differentially expressed in tumor cells, and antibodies immunospecific for the protein, to treat, diagnose and/or prevent said cancers, are provided for by the present invention.

3 Claims, 9 Drawing Sheets

1) H69
2) H82
3) GLC-1
4) GLC-M13
5) SH-SYSY
6) CCI
7) Blanc

Fig. 4
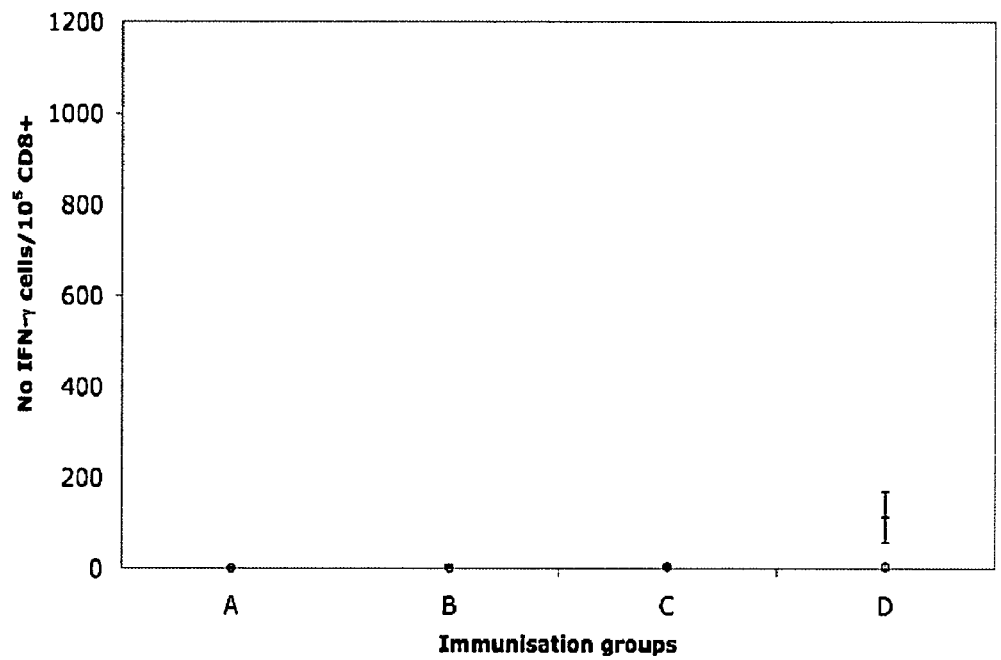
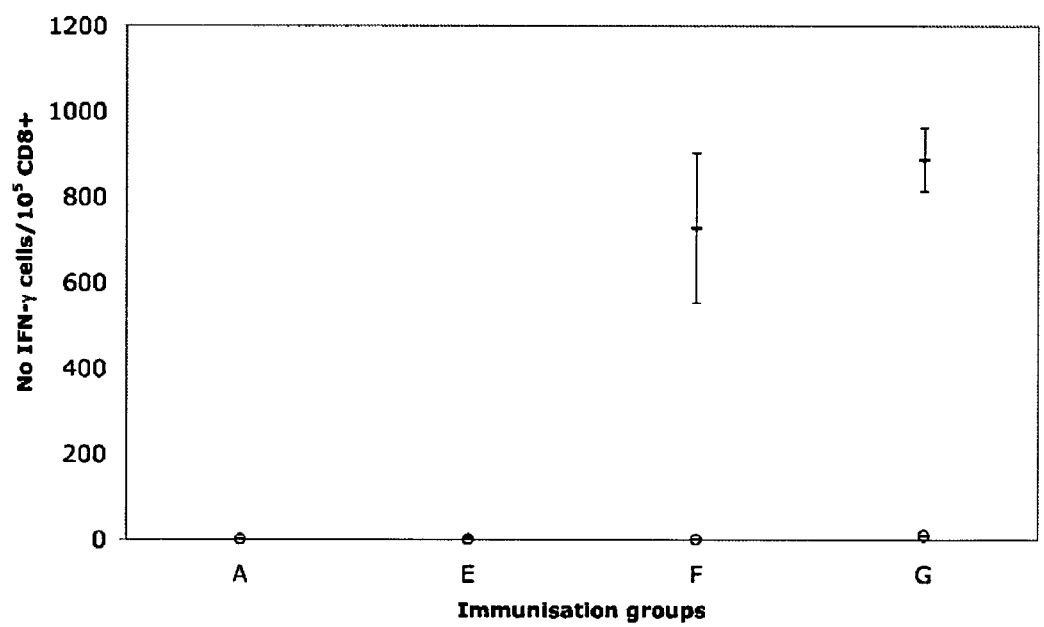

Fig. 6 - A
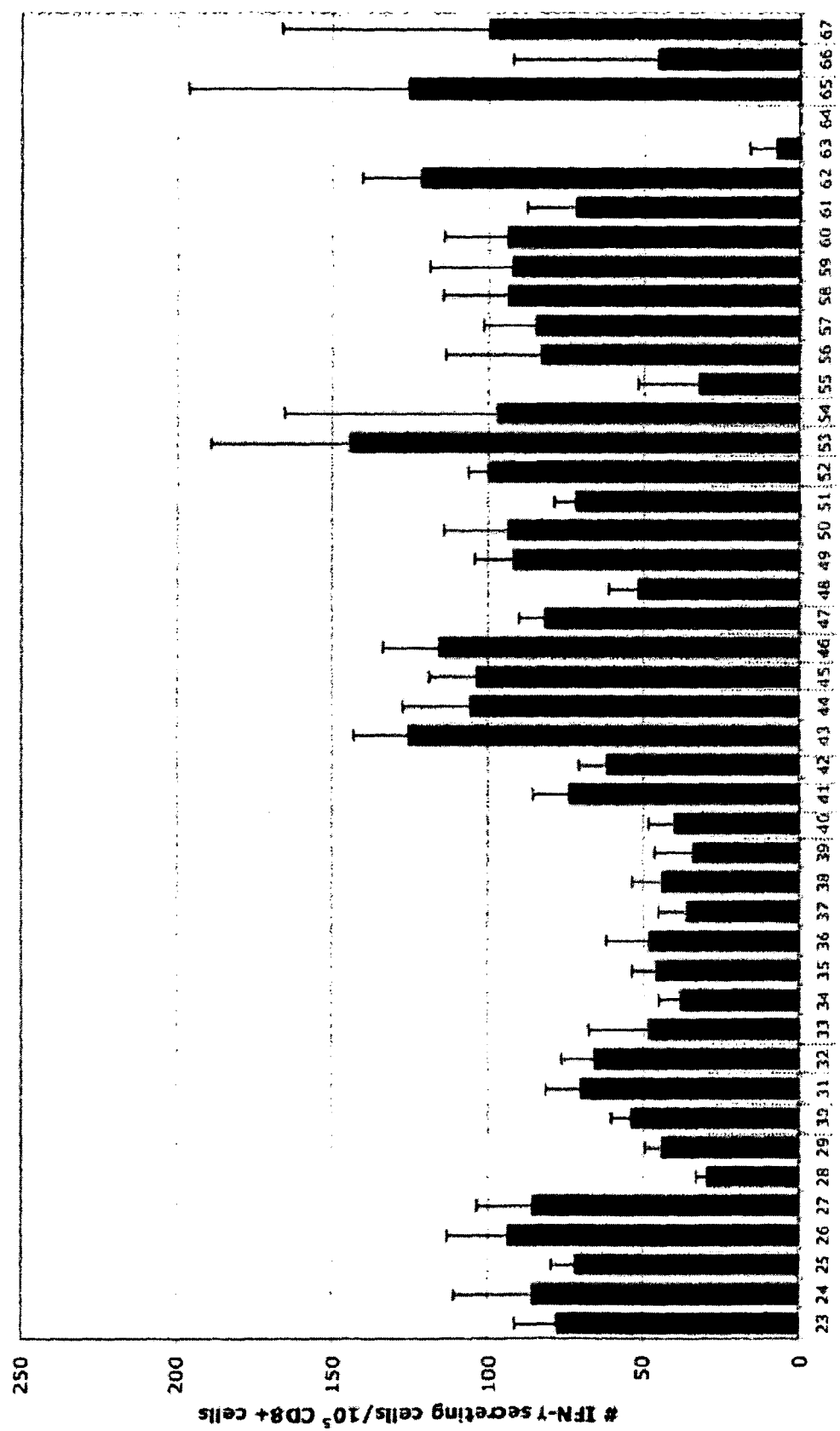

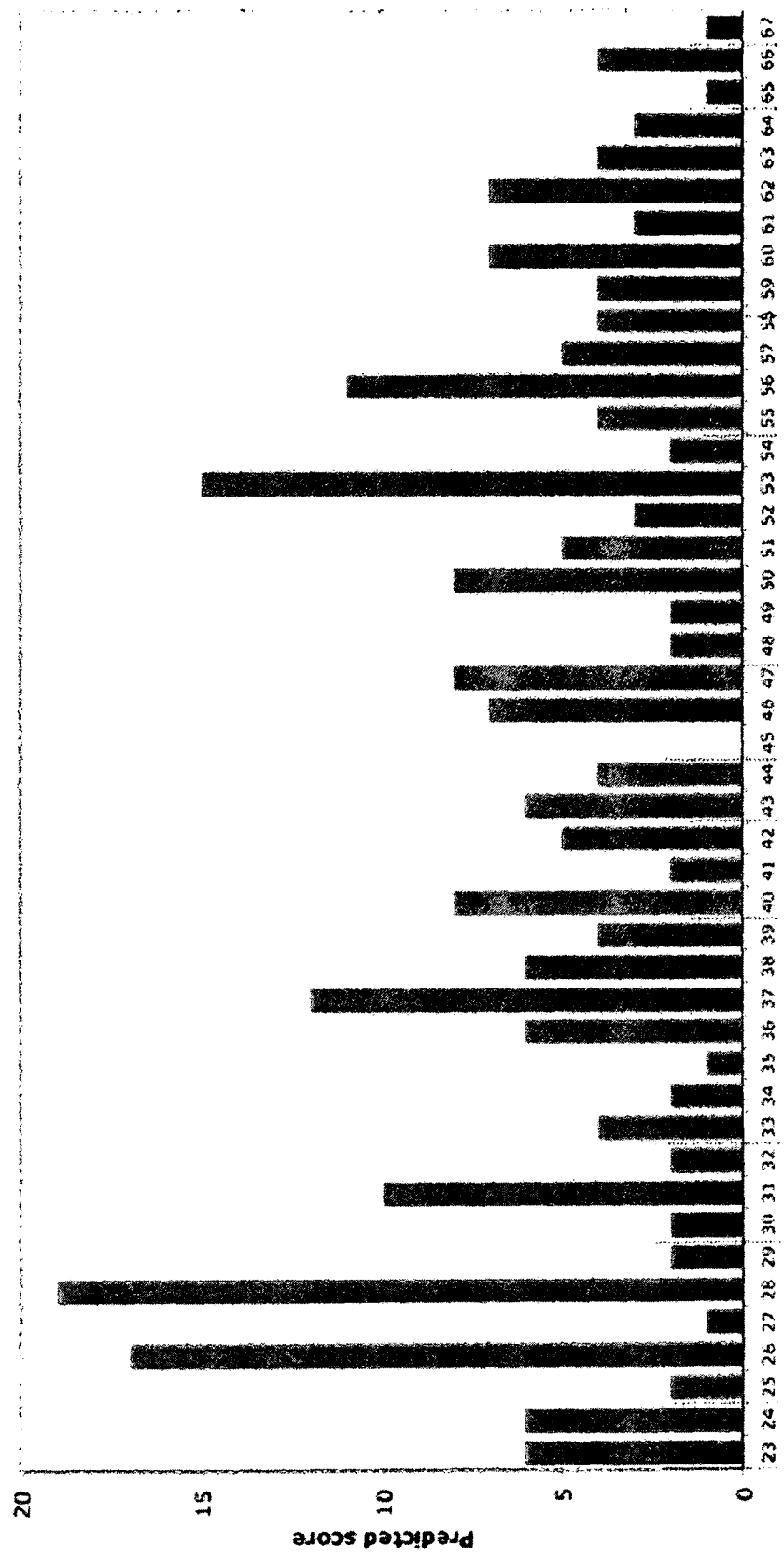
Fig.6 - B

Fig. 7
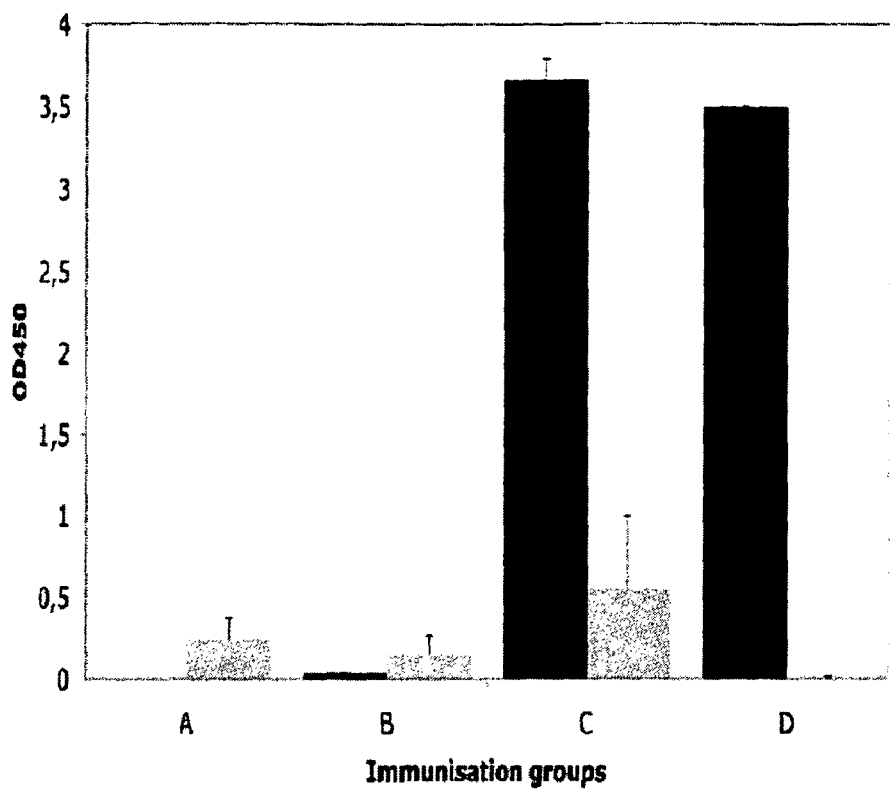
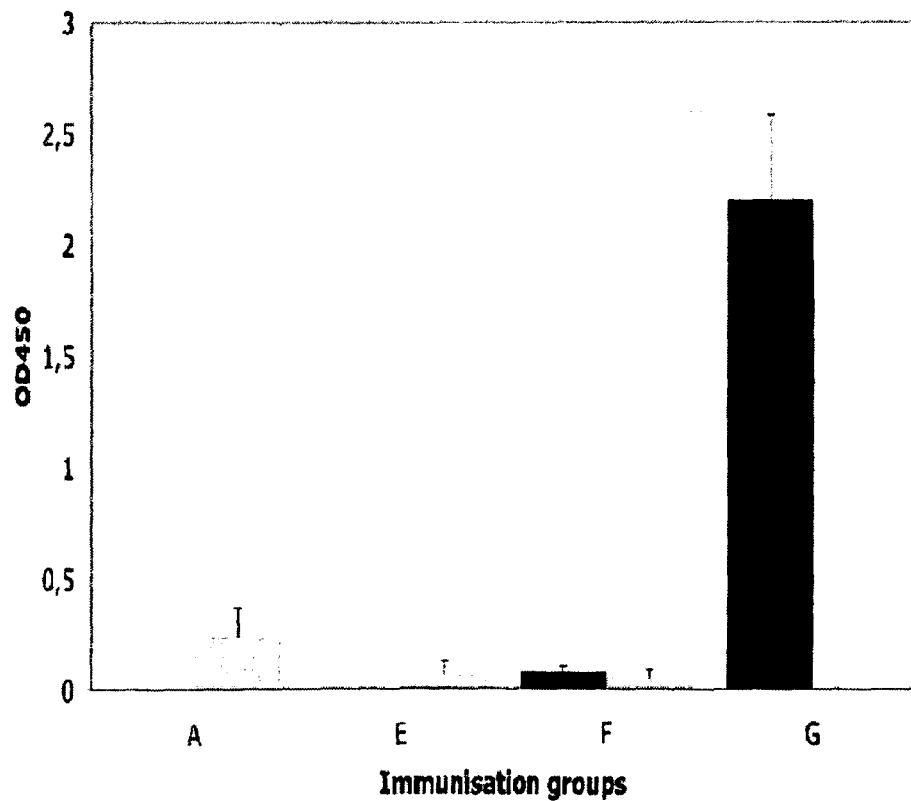

Fig. 8
A
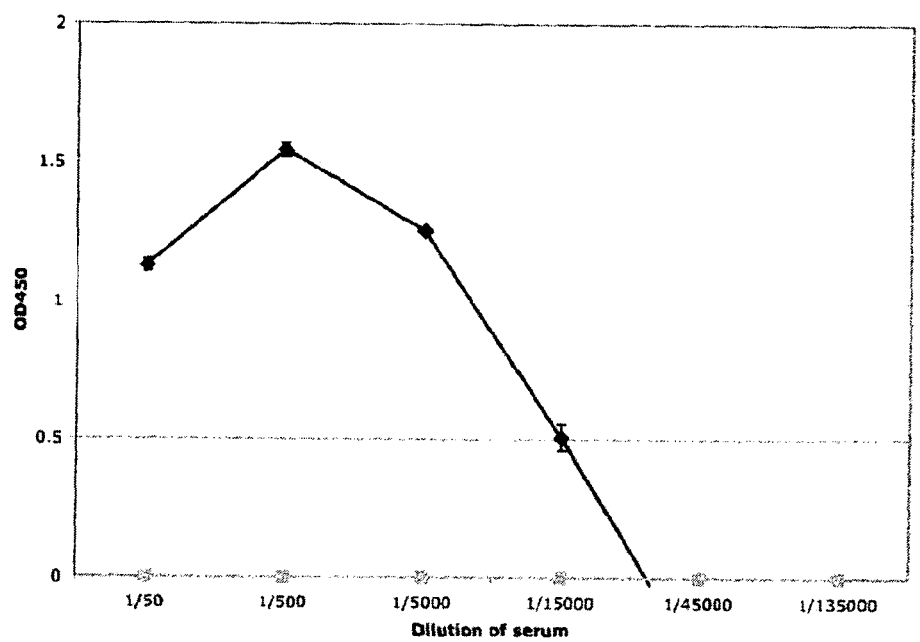
B
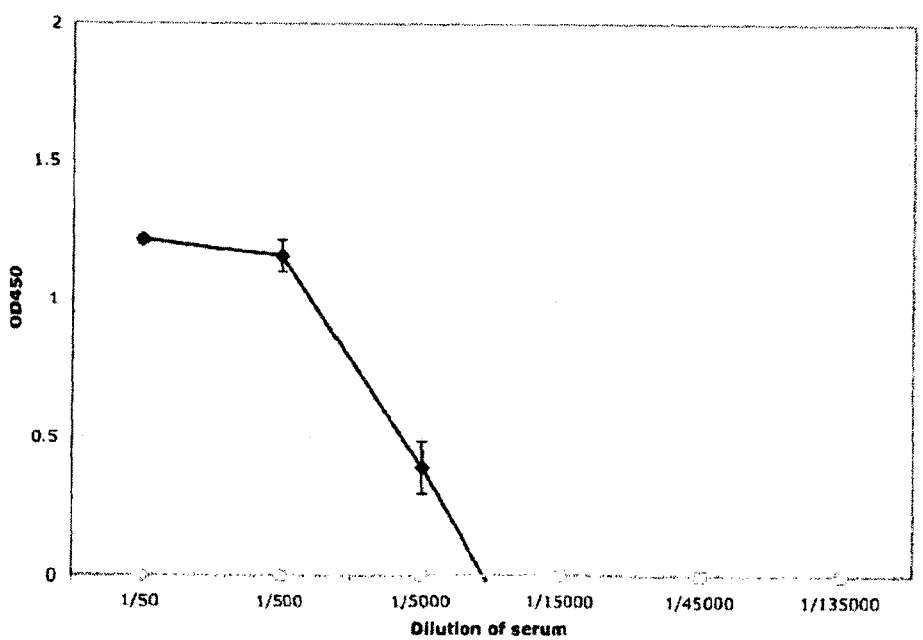

SEQUENCE LISTING

<160> NUMBER OF SEQ ID NOS: 50

<210> SEQ ID NO 1
<211> LENGTH: 813
<212> TYPE: DNA
<213> ORGANISM: Homo Sapiens
<220> FEATURE:
<221> NAME/KEY: CDS
<222> LOCATION: (1)..(813)

<400> SEQUENCE: 1

```
ctg cct gcc gac act acg gcc act gtc gag gac atg ctg cct tct gtc      48
Leu Pro Ala Asp Thr Thr Ala Thr Val Glu Asp Met Leu Pro Ser Val
1               5                   10                  15 acc acc gtc acc act aac tct gac act atc acc gaa acc ttt gcc act      96
Thr Thr Val Thr Thr Asn Ser Asp Thr Ile Thr Glu Thr Phe Ala Thr
            20                  25                  30 gct cag aac agc ccc acc agt gag acc acc acc ctg acc tcc agt att     144
Ala Gln Asn Ser Pro Thr Ser Glu Thr Thr Thr Leu Thr Ser Ser Ile
        35                  40                  45 gcc ccg ccg acg gcc acg cct gac tca aac tct gta ccg gct ggc         192
Ala Pro Pro Ala Thr Ala Thr Pro Asp Ser Asn Ser Val Pro Ala Gly
    50                  55                  60 cag gcc acc cct tcc aag ggg ccc agc gcc tct gcc ccc tcc ccg gcc     240
Gln Ala Thr Pro Ser Lys Gly Pro Ser Ala Ser Ala Pro Ser Pro Ala
65                  70                  75                  80 cca gct tca gcc ccc aag gtc gcc ccc ctc gtt gac ctg agc gac acc     288
Pro Ala Ser Ala Pro Lys Val Ala Pro Leu Val Asp Leu Ser Asp Thr
                85                  90                  95 ccg acc tca acc cct gcc gct agc aat ttg tct tct agt gtc ctg gct     336
Pro Thr Ser Thr Pro Ala Ala Ser Asn Leu Ser Ser Ser Val Leu Ala
            100                 105                 110 aac caa ggg gct gtc ctc agc cca agc gcc cct gct ggt gtc ggg gag     384
Asn Gln Gly Ala Val Leu Ser Pro Ser Ala Pro Ala Gly Val Gly Glu
        115                 120                 125 gcc tct aag gct cct ccg gcc agc aag ccc acc cct gca cca gtc ccc     432
Ala Ser Lys Ala Pro Pro Ala Ser Lys Pro Thr Pro Ala Pro Val Pro
    130                 135                 140 acc ccg act ggg gca gcc agt cct cta gca gca gcg gct gcc cct gcc     480
Thr Pro Thr Gly Ala Ala Ser Pro Leu Ala Ala Ala Ala Pro Ala
145                 150                 155                 160
```

```
aca gaa gcc cct cag gcc aag cag gag gct ccc agc acc aaa ggc ccg      528
Thr Glu Ala Pro Gln Ala Lys Gln Glu Ala Pro Ser Thr Lys Gly Pro
                165                 170                 175 gac ccg gag ccc acc cag ccc gga gcc gcg aag agc ccg gcc gag gca      576
Asp Pro Glu Pro Thr Gln Pro Gly Ala Ala Lys Ser Pro Ala Glu Ala
            180                 185                 190 gcc aca gcc ctt gct agc ccg aag agc gag gct gcc tcc gtc agc acc      624
Ala Thr Ala Leu Ala Ser Pro Lys Ser Glu Ala Ala Ser Val Ser Thr
        195                 200                 205 aca aac cct tcc cag ggc gag gac ttt aaa atg gac gaa ggg aac ttc      672
Thr Asn Pro Ser Gln Gly Glu Asp Phe Lys Met Asp Glu Gly Asn Phe
    210                 215                 220 aag acc cca gat att gac ctt gca aag gat gtt ttt gca gcc ctg ggc      720
Lys Thr Pro Asp Ile Asp Leu Ala Lys Asp Val Phe Ala Ala Leu Gly
225                 230                 235                 240 tct cct gct ccc gcc gct ggg gcc agt gga caa gcc cct gag ctt gct      768
Ser Pro Ala Pro Ala Ala Gly Ala Ser Gly Gln Ala Pro Glu Leu Ala
                245                 250                 255 cct tcc act gca gac agc tct gtt tcg cct gcg cca gca aag acg          813
Pro Ser Thr Ala Asp Ser Ser Val Ser Pro Ala Pro Ala Lys Thr
            260                 265                 270

<210> SEQ ID NO 2
<211> LENGTH: 271
<212> TYPE: PRT
<213> ORGANISM: Homo Sapiens

<400> SEQUENCE: 2

Leu Pro Ala Asp Thr Thr Ala Thr Val Glu Asp Met Leu Pro Ser Val
1               5                   10                  15

Thr Thr Val Thr Thr Asn Ser Asp Thr Ile Thr Glu Thr Phe Ala Thr
            20                  25                  30

Ala Gln Asn Ser Pro Thr Ser Glu Thr Thr Thr Leu Thr Ser Ser Ile
        35                  40                  45

Ala Pro Pro Ala Thr Ala Thr Pro Asp Ser Asn Ser Val Pro Ala Gly
    50                  55                  60

Gln Ala Thr Pro Ser Lys Gly Pro Ser Ala Ser Ala Pro Ser Pro Ala
65                  70                  75                  80

Pro Ala Ser Ala Pro Lys Val Ala Pro Leu Val Asp Leu Ser Asp Thr
                85                  90                  95

Pro Thr Ser Thr Pro Ala Ala Ser Asn Leu Ser Ser Ser Val Leu Ala
            100                 105                 110

Asn Gln Gly Ala Val Leu Ser Pro Ser Ala Pro Ala Gly Val Gly Glu
        115                 120                 125

Ala Ser Lys Ala Pro Pro Ala Ser Lys Pro Thr Pro Ala Pro Val Pro
    130                 135                 140

Thr Pro Thr Gly Ala Ala Ser Pro Leu Ala Ala Ala Ala Pro Ala
145                 150                 155                 160

Thr Glu Ala Pro Gln Ala Lys Gln Glu Ala Pro Ser Thr Lys Gly Pro
                165                 170                 175

Asp Pro Glu Pro Thr Gln Pro Gly Ala Ala Lys Ser Pro Ala Glu Ala
            180                 185                 190

Ala Thr Ala Leu Ala Ser Pro Lys Ser Glu Ala Ala Ser Val Ser Thr
        195                 200                 205

Thr Asn Pro Ser Gln Gly Glu Asp Phe Lys Met Asp Glu Gly Asn Phe
    210                 215                 220

Lys Thr Pro Asp Ile Asp Leu Ala Lys Asp Val Phe Ala Ala Leu Gly
```

```
                 225                 230                 235                 240
Ser Pro Ala Pro Ala Ala Gly Ala Ser Gly Gln Ala Pro Glu Leu Ala
            245                 250                 255
Pro Ser Thr Ala Asp Ser Ser Val Ser Pro Ala Pro Ala Lys Thr
        260                 265                 270

<210> SEQ ID NO 3
<211> LENGTH: 3588
<212> TYPE: DNA
<213> ORGANISM: Homo Sapiens

<400> SEQUENCE: 3
```

| | | | | | |
|---|---|---|---|---|---|
| gaattcgagg | atccgggtac | catggcgcgt | gaacgcagct | cggctgccgc | tggcaggaaa | 60 |
| caattctgca | aaataatca | tactcagcct | ggcaattgtc | tgccctagg | tctgtcgctc | 120 |
| agccgccgtc | cacactcgct | gcagggggg | gggcacagaa | tttaccgcgg | caagaacatc | 180 |
| cctcccagcc | agcagattac | aatgctgcaa | actaaggatc | tcatctggac | tttgtttttc | 240 |
| ctgggaactg | cagtttctct | gcaggtggat | attgttccca | gccaggggga | gatcagcgtt | 300 |
| ggagagtcca | aattcttctt | atgccaagtg | gcaggagatg | ccaaagataa | agacatctcc | 360 |
| tggttctccc | ccaatggaga | aaagctcacc | ccaaaccagc | agcggatctc | agtggtgtgg | 420 |
| aatgatgatt | cctcctccac | cctcaccatc | tataacgcca | acatcgacga | cgccggcatt | 480 |
| tacaagtgtg | tggttacagg | cgaggatggc | agtgagtcag | aggccaccgt | caacgtgaag | 540 |
| atctttcaga | agctcatgtt | caagaatgcg | ccaacccccac | aggagttccg | ggagggggaa | 600 |
| gatgccgtga | ttgtgtgtga | tgtggtcagc | tccctcccac | caaccatcat | ctggaaacac | 660 |
| aaaggccgag | atgtcatcct | gaaaaagat | gtccgattca | tagtcctgtc | caacaactac | 720 |
| ctgcagatcc | ggggcatcaa | gaaaacagat | gagggcactt | atcgctgtga | gggcagaatc | 780 |
| ctggcacggg | gggagatcaa | cttcaaggac | attcaggtca | ttgtgaatgt | gccacctacc | 840 |
| atccaggcca | ggcagaatat | tgtgaatgcc | accgccaacc | tcggccagtc | cgtcacccctg | 900 |
| gtgtgcgatg | ccgaaggctt | cccagagccc | accatgagct | ggacaaagga | tggggaacag | 960 |
| atagagcaag | aggaagacga | tgagaagtac | atcttcagcg | acgatagttc | ccagctgacc | 1020 |
| atcaaaaagg | tggataagaa | cgacgaggct | gagtacatct | gcattgctga | aaacaaggct | 1080 |
| ggcgagcagg | atgcgaccat | ccacctcaaa | gtctttgcaa | acccaaaat | cacatatgta | 1140 |
| gagaaccaga | ctgccatgga | attagaggag | caggtcactc | ttacctgtga | agcctccgga | 1200 |
| gaccccattc | cctccatcac | ctggaggact | tctacccgga | acatcagcag | cgaagaaaag | 1260 |
| gcttcgtgga | ctcgaccaga | gaagcaagag | actctggatg | gcacatggt | ggtgcgtagc | 1320 |
| catgcccgtg | tgtcgtcgct | gaccctgaag | agcatccagt | acactgatgc | cggagagtac | 1380 |
| atctgcaccg | ccagcaacac | catcggccag | gactcccagt | ccatgtacct | tgaagtgcaa | 1440 |
| tatgccccaa | agctacaggg | ccctgtggct | gtgtacactt | gggagggaa | ccaggtgaac | 1500 |
| atcacctgcg | aggtatttgc | ctatcccagt | gccacgatct | catggtttcg | ggatggccag | 1560 |
| ctgctgccaa | gctccaatta | cagcaatatc | aagatctaca | caccccctc | tgccagctat | 1620 |
| ctggaggtga | ccccagactc | tgagaatgat | tttgggaact | acaactgtac | tgcagtgaac | 1680 |
| cgcattgggc | aggagtcctt | ggaattcatc | cttgttcaag | cagacacccc | ctcttccacca | 1740 |
| tccatcgacc | aggtggagcc | atactccagc | acagcccagg | tgcagtttga | tgaaccagag | 1800 |
| gccacaggtg | gggtgcccat | cctcaaatac | aaagctgagt | ggagagcagt | tggtgaagaa | 1860 |
| gtatggcatt | ccaagtggta | tgatgccaag | gaagccagca | tggagggcat | cgtcaccatc | 1920 |

-continued

| | |
|---|---|
| gtgggcctga agcccgaaac aacgtacgcc gtaaggctgg cggcgctcaa tggcaaaggg | 1980 |
| ctgggtgaga tcagcgcggc ctccgagttc aagacgcagc cagtccaagg ggaacccagt | 2040 |
| gcacctaagc tcgaagggca gatgggagag gatggaaact ctattaaagt gaacctgatc | 2100 |
| aagcaggatg acggcggctc ccccatcaga cactatctgg tcaggtaccg agcgctctcc | 2160 |
| tccgagtgga aaccagagat caggctcccg tctggcagtg accacgtcat gctgaagtcc | 2220 |
| ctggactgga atgctgagta tgaggtctac gtggtggctg agaaccagca aggaaaatcc | 2280 |
| aaggcggctc attttgtgtt caggacctcg gcccagccca cagccatccc agccaacggc | 2340 |
| agccccacct caggcctgag caccggggcc atcgtgggca tcctcatcgt catcttcgtc | 2400 |
| ctgctcctgg tggttgtgga catcacctgc tacttcctga caagtgtgg cctgttcatg | 2460 |
| tgcattgcgg tcaacctgtg tggaaaagcc gggcccgggg ccaagggcaa ggacatggag | 2520 |
| gagggcaagg ccgccttctc gaaagatgag tccaaggagc ccatcgtgga ggttcgaacg | 2580 |
| gaggaggaga ggaccccaaa ccatgatgga gggaaacaca cagagcccaa cgagaccacg | 2640 |
| ccactgacgg agcccgagct gcctgccgac actacggcca ctgtcgagga catgctgcct | 2700 |
| tctgtcacca ccgtcaccac taactctgac actatcaccg aaacctttgc cactgctcag | 2760 |
| aacagcccca ccagtgagac caccaccctg acctccagta ttgccccgcc ggccacggcc | 2820 |
| acgcctgact caaactctgt accggctggc caggccaccc cttccaaggg gcccagcgcc | 2880 |
| tctgcccct cccggcccc agcttcagcc cccaaggtcg ccccctcgt tgacctgagc | 2940 |
| gacaccccga cctcaacccc tgccgctagc aatttgtctt ctagtgtcct ggctaaccaa | 3000 |
| ggggctgtcc tcagcccaag cgcccctgct ggtgtcgggg aggcctctaa ggctcctccg | 3060 |
| gccagcaagc ccacccctgc accagtcccc accccgactg gggcagccag tcctctagca | 3120 |
| gcagcggctg cccctgccac agaagcccct caggccaagc aggaggctcc cagcaccaaa | 3180 |
| ggcccgacc cggagcccac ccagcccgga gccgcgaaga gcccggccga ggcagccaca | 3240 |
| gcccttgcta gcccgaagag cgaggctgcc tccgtcagca ccacaaaccc ttcccagggc | 3300 |
| gaggacttta aaatggacga agggaacttc aagaccccag atattgacct tgcaaaggat | 3360 |
| gttttttgcag ccctgggctc tcctgctccc gccgctgggg ccagtggaca agcccctgag | 3420 |
| cttgctcctt ccactgcaga cagctctgtt tcgcctgcgc cagcaaagac gaagggcccc | 3480 |
| gtagaagcaa agccagagtg ccaggagaca gaaacgaagc cagcgccagc cgaagtcaag | 3540 |
| acggtcccca tgacgccac acagacaaag gagaacgaga gcaaagca | 3588 |

<210> SEQ ID NO 4
<211> LENGTH: 1186
<212> TYPE: PRT
<213> ORGANISM: Homo Sapiens

<400> SEQUENCE: 4

Glu Phe Glu Asp Pro Gly Thr Met Ala Arg Glu Arg Ser Ser Ala Ala
1               5                   10                  15

Ala Gly Arg Lys Gln Phe Cys Lys Asn Asn His Thr Gln Pro Gly Asn
            20                  25                  30

Cys Leu Pro Leu Gly Leu Ser Leu Ser Arg Arg Pro His Ser Leu Gln
        35                  40                  45

Gly Gly Gly His Arg Ile Tyr Arg Gly Lys Asn Ile Pro Pro Ser Gln
    50                  55                  60

Gln Ile Thr Met Leu Gln Thr Lys Asp Leu Ile Trp Thr Leu Phe Phe
65                  70                  75                  80

Leu Gly Thr Ala Val Ser Leu Gln Val Asp Ile Val Pro Ser Gln Gly

```
                85                  90                  95
Glu Ile Ser Val Gly Glu Ser Lys Phe Phe Leu Cys Gln Val Ala Gly
                100                 105                 110
Asp Ala Lys Asp Lys Asp Ile Ser Trp Phe Ser Pro Asn Gly Glu Lys
            115                 120                 125
Leu Thr Pro Asn Gln Gln Arg Ile Ser Val Val Trp Asn Asp Asp Ser
        130                 135                 140
Ser Ser Thr Leu Thr Ile Tyr Asn Ala Asn Ile Asp Asp Ala Gly Ile
145                 150                 155                 160
Tyr Lys Cys Val Val Thr Gly Glu Asp Gly Ser Glu Ser Glu Ala Thr
                165                 170                 175
Val Asn Val Lys Ile Phe Gln Lys Leu Met Phe Lys Asn Ala Pro Thr
            180                 185                 190
Pro Gln Glu Phe Arg Glu Gly Glu Asp Ala Val Ile Val Cys Asp Val
        195                 200                 205
Val Ser Ser Leu Pro Pro Thr Ile Ile Trp Lys His Lys Gly Arg Asp
210                 215                 220
Val Ile Leu Lys Lys Asp Val Arg Phe Ile Val Leu Ser Asn Asn Tyr
225                 230                 235                 240
Leu Gln Ile Arg Gly Ile Lys Lys Thr Asp Glu Gly Thr Tyr Arg Cys
                245                 250                 255
Glu Gly Arg Ile Leu Ala Arg Gly Glu Ile Asn Phe Lys Asp Ile Gln
            260                 265                 270
Val Ile Val Asn Val Pro Pro Thr Ile Gln Ala Arg Gln Asn Ile Val
        275                 280                 285
Asn Ala Thr Ala Asn Leu Gly Gln Ser Val Thr Leu Val Cys Asp Ala
290                 295                 300
Glu Gly Phe Pro Glu Pro Thr Met Ser Trp Thr Lys Asp Gly Glu Gln
305                 310                 315                 320
Ile Glu Gln Glu Glu Asp Asp Glu Lys Tyr Ile Phe Ser Asp Asp Ser
                325                 330                 335
Ser Gln Leu Thr Ile Lys Lys Val Asp Lys Asn Asp Glu Ala Glu Tyr
            340                 345                 350
Ile Cys Ile Ala Glu Asn Lys Ala Gly Glu Gln Asp Ala Thr Ile His
        355                 360                 365
Leu Lys Val Phe Ala Lys Pro Lys Ile Thr Tyr Val Glu Asn Gln Thr
    370                 375                 380
Ala Met Glu Leu Glu Glu Gln Val Thr Leu Thr Cys Glu Ala Ser Gly
385                 390                 395                 400
Asp Pro Ile Pro Ser Ile Thr Trp Arg Thr Ser Thr Arg Asn Ile Ser
                405                 410                 415
Ser Glu Glu Lys Thr Leu Asp Gly His Met Val Val Arg Ser His Ala
            420                 425                 430
Arg Val Ser Ser Leu Thr Leu Lys Ser Ile Gln Tyr Thr Asp Ala Gly
        435                 440                 445
Glu Tyr Ile Cys Thr Ala Ser Asn Thr Ile Gly Gln Asp Ser Gln Ser
    450                 455                 460
Met Tyr Leu Glu Val Gln Tyr Ala Pro Lys Leu Gln Gly Pro Val Ala
465                 470                 475                 480
Val Tyr Thr Trp Glu Gly Asn Gln Val Asn Ile Thr Cys Glu Val Phe
                485                 490                 495
Ala Tyr Pro Ser Ala Thr Ile Ser Trp Phe Arg Asp Gly Gln Leu Leu
            500                 505                 510
```

-continued

```
Pro Ser Ser Asn Tyr Ser Asn Ile Lys Ile Tyr Asn Thr Pro Ser Ala
        515                 520                 525

Ser Tyr Leu Glu Val Thr Pro Asp Ser Glu Asn Asp Phe Gly Asn Tyr
        530                 535                 540

Asn Cys Thr Ala Val Asn Arg Ile Gly Gln Glu Ser Leu Glu Phe Ile
545                 550                 555                 560

Leu Val Gln Ala Asp Thr Pro Ser Ser Pro Ser Ile Asp Gln Val Glu
                565                 570                 575

Pro Tyr Ser Ser Thr Ala Gln Val Gln Phe Asp Glu Pro Glu Ala Thr
            580                 585                 590

Gly Gly Val Pro Ile Leu Lys Tyr Lys Ala Glu Trp Arg Ala Val Gly
        595                 600                 605

Glu Glu Val Trp His Ser Lys Trp Tyr Asp Ala Lys Glu Ala Ser Met
    610                 615                 620

Glu Gly Ile Val Thr Ile Val Gly Leu Lys Pro Glu Thr Thr Tyr Ala
625                 630                 635                 640

Val Arg Leu Ala Ala Leu Asn Gly Lys Gly Leu Gly Glu Ile Ser Ala
                645                 650                 655

Ala Ser Glu Phe Lys Thr Gln Pro Val Gln Gly Glu Pro Ser Ala Pro
            660                 665                 670

Lys Leu Glu Gly Gln Met Gly Glu Asp Gly Asn Ser Ile Lys Val Asn
        675                 680                 685

Leu Ile Lys Gln Asp Asp Gly Gly Ser Pro Ile Arg His Tyr Leu Val
    690                 695                 700

Arg Tyr Arg Ala Leu Ser Ser Glu Trp Lys Pro Glu Ile Arg Leu Pro
705                 710                 715                 720

Ser Gly Ser Asp His Val Met Leu Lys Ser Leu Asp Trp Asn Ala Glu
                725                 730                 735

Tyr Glu Val Tyr Val Val Ala Glu Asn Gln Gln Gly Lys Ser Lys Ala
            740                 745                 750

Ala His Phe Val Phe Arg Thr Ser Ala Gln Pro Thr Ala Ile Pro Ala
        755                 760                 765

Asn Gly Ser Pro Thr Ser Gly Leu Ser Thr Gly Ala Ile Val Gly Ile
    770                 775                 780

Leu Ile Val Ile Phe Val Leu Leu Val Val Val Asp Ile Thr Cys
785                 790                 795                 800

Tyr Phe Leu Asn Lys Cys Gly Leu Phe Met Cys Ile Ala Val Asn Leu
                805                 810                 815

Cys Gly Lys Ala Gly Pro Gly Ala Lys Gly Lys Asp Met Glu Glu Gly
            820                 825                 830

Lys Ala Ala Phe Ser Lys Asp Glu Ser Lys Glu Pro Ile Val Glu Val
        835                 840                 845

Arg Thr Glu Glu Glu Arg Thr Pro Asn His Asp Gly Gly Lys His Thr
    850                 855                 860

Glu Pro Asn Glu Thr Thr Pro Leu Thr Glu Pro Glu Leu Pro Ala Asp
865                 870                 875                 880

Thr Thr Ala Thr Val Glu Asp Met Leu Pro Ser Val Thr Thr Val Thr
                885                 890                 895

Thr Asn Ser Asp Thr Ile Thr Glu Thr Phe Ala Thr Ala Gln Asn Ser
            900                 905                 910

Pro Thr Ser Glu Thr Thr Thr Leu Thr Ser Ser Ile Ala Pro Pro Ala
        915                 920                 925

Thr Ala Thr Pro Asp Ser Asn Ser Val Pro Ala Gly Gln Ala Thr Pro
    930                 935                 940
```

Ser Lys Gly Pro Ser Ala Ser Ala Pro Ser Pro Ala Pro Ala Ser Ala
945                 950                 955                 960

Pro Lys Val Ala Pro Leu Val Asp Leu Ser Asp Thr Pro Thr Ser Thr
                965                 970                 975

Pro Ala Ala Ser Asn Leu Ser Ser Ser Val Leu Ala Asn Gln Gly Ala
            980                 985                 990

Val Leu Ser Pro Ser Ala Pro Ala Gly Val Gly Glu Ala Ser Lys Ala
        995                 1000                1005

Pro Pro Ala Ser Lys Pro Thr Pro Ala Pro Val Pro Thr Pro Thr
    1010                1015                1020

Gly Ala Ala Ser Pro Leu Ala Ala Ala Ala Pro Ala Thr Glu
    1025                1030                1035

Ala Pro Gln Ala Lys Gln Glu Ala Pro Ser Thr Lys Gly Pro Asp
    1040                1045                1050

Pro Glu Pro Thr Gln Pro Gly Ala Ala Lys Ser Pro Ala Glu Ala
    1055                1060                1065

Ala Thr Ala Leu Ala Ser Pro Lys Ser Glu Ala Ala Ser Val Ser
    1070                1075                1080

Thr Thr Asn Pro Ser Gln Gly Glu Asp Phe Lys Met Asp Glu Gly
    1085                1090                1095

Asn Phe Lys Thr Pro Asp Ile Asp Leu Ala Lys Asp Val Phe Ala
    1100                1105                1110

Ala Leu Gly Ser Pro Ala Pro Ala Ala Gly Ala Ser Gly Gln Ala
    1115                1120                1125

Pro Glu Leu Ala Pro Ser Thr Ala Asp Ser Ser Val Ser Pro Ala
    1130                1135                1140

Pro Ala Lys Thr Lys Gly Pro Val Glu Ala Lys Pro Glu Cys Gln
    1145                1150                1155

Glu Thr Glu Thr Lys Pro Ala Pro Ala Glu Val Lys Thr Val Pro
    1160                1165                1170

Asn Asp Ala Thr Gln Thr Lys Glu Asn Glu Ser Lys Ala
    1175                1180                1185

<210> SEQ ID NO 5
<211> LENGTH: 372
<212> TYPE: DNA
<213> ORGANISM: Homo Sapiens

<400> SEQUENCE: 5
gccgctagca atttgtcttc tagtgtcctg gctaaccaag gggctgtcct cagcccaagc      60
gcccctgctg gtgtcgggga ggcctctaag gctcctccgg ccagcaagcc acccctgca     120 ccagtcccca ccccgactgg ggcagccagt cctctagcag cagcggctgc ccctgccaca     180
gaagcccctc aggccaagca ggaggctccc agcaccaaag gcccggaccc ggagcccacc     240
cagcccggag ccgcgaagag cccggccgag gcagccacag cccttgctag cccgaagagc     300
gaggctgcct ccgtcagcac cacaaaccct tcccagggcg aggactttaa aatggacgaa     360
gggaacttca ag                                                         372

<210> SEQ ID NO 6
<211> LENGTH: 124
<212> TYPE: PRT
<213> ORGANISM: Homo Sapiens

<400> SEQUENCE: 6

Ala Ala Ser Asn Leu Ser Ser Ser Val Leu Ala Asn Gln Gly Ala Val

```
                1               5                   10                  15
Leu Ser Pro Ser Ala Pro Ala Gly Val Gly Glu Ala Ser Lys Ala Pro
                20                  25                  30

Pro Ala Ser Lys Pro Thr Pro Ala Pro Val Pro Thr Pro Thr Gly Ala
                35                  40                  45

Ala Ser Pro Leu Ala Ala Ala Ala Pro Ala Thr Glu Ala Pro Gln
            50                  55                  60

Ala Lys Gln Glu Ala Pro Ser Thr Lys Gly Pro Asp Pro Glu Pro Thr
65                  70                  75                  80

Gln Pro Gly Ala Ala Lys Ser Pro Ala Glu Ala Thr Ala Leu Ala
                85                  90                  95

Ser Pro Lys Ser Glu Ala Ala Ser Val Ser Thr Thr Asn Pro Ser Gln
                100                 105                 110

Gly Glu Asp Phe Lys Met Asp Glu Gly Asn Phe Lys
                115                 120
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 7

```
Pro Leu Val Asp Leu Ser Asp Thr Pro
1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 8

```
Leu Ser Asp Thr Pro Thr Ser Thr Pro
1               5
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 9

```
Pro Thr Ser Thr Pro Ala Ala Ser Asn
1               5
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 10

```
Pro Ala Ala Ser Asn Leu Ser Ser Ser
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 11

Asn Leu Ser Ser Ser Val Leu Ala Asn
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 12

Ser Val Leu Ala Asn Gln Gly Ala Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 13

Asn Gln Gly Ala Val Leu Ser Pro Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 14

Val Leu Ser Pro Ser Ala Pro Ala Gly
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 15

Ser Ala Pro Ala Gly Val Gly Glu Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 16
```

```
Gly Val Gly Glu Ala Ser Lys Ala Pro
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 17

Ala Ser Lys Ala Pro Pro Ala Ser Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 18

Pro Pro Ala Ser Lys Pro Thr Pro Ala
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 19

Lys Pro Thr Pro Ala Pro Val Pro Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 20

Ala Pro Val Pro Thr Pro Thr Gly Ala
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 21

Thr Pro Thr Gly Ala Ala Ser Pro Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
```

9-mer MUM peptide

<400> SEQUENCE: 22

Ala Ala Ser Pro Leu Ala Ala Ala Ala
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 23

Leu Ala Ala Ala Ala Ala Pro Ala Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 24

Ala Ala Pro Ala Thr Glu Ala Pro Gln
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 25

Thr Glu Ala Pro Gln Ala Lys Gln Glu
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 26

Gln Ala Lys Gln Glu Ala Pro Ser Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 27

Glu Ala Pro Ser Thr Lys Gly Pro Asp
1               5

<210> SEQ ID NO 28
<211> LENGTH: 9

```
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 28

Thr Lys Gly Pro Asp Pro Glu Pro Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 29

Asp Pro Glu Pro Thr Gln Pro Gly Ala
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 30

Thr Gln Pro Gly Ala Ala Lys Ser Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 31

Ala Ala Lys Ser Pro Ala Glu Ala Ala
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 32

Pro Ala Glu Ala Ala Thr Ala Leu Ala
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 33

Ala Thr Ala Leu Ala Ser Pro Lys Ser
1               5
```

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 34

Ala Ser Pro Lys Ser Glu Ala Ala Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 35

Ser Glu Ala Ala Ser Val Ser Thr Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 36

Ser Val Ser Thr Thr Asn Pro Ser Gln
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 37

Thr Asn Pro Ser Gln Gly Glu Asp Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 38

Gln Gly Glu Asp Phe Lys Met Asp Glu
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide
```

-continued

```
<400> SEQUENCE: 39

Phe Lys Met Asp Glu Gly Asn Phe Lys
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 40

Glu Gly Asn Phe Lys Thr Pro Asp Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 41

Lys Thr Pro Asp Ile Asp Leu Ala Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 42

Ile Asp Leu Ala Lys Asp Val Phe Ala
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 43

Lys Asp Val Phe Ala Ala Leu Gly Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 44

Ala Ala Leu Gly Ser Pro Ala Pro Ala
1               5

<210> SEQ ID NO 45
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      9-mer MUM peptide

<400> SEQUENCE: 45

Ser Pro Ala Pro Ala Ala Gly Ala Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 46

Ala Ala Gly Ala Ser Gly Gln Ala Pro
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 47

Ser Gly Gln Ala Pro Glu Leu Ala Pro
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 48

Pro Glu Leu Ala Pro Ser Thr Ala Asp
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 49

Pro Ser Thr Ala Asp Ser Ser Val Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      9-mer MUM peptide

<400> SEQUENCE: 50

Asp Ser Ser Val Ser Pro Ala Pro Ala
1               5
```

CANCER VACCINE

CLAIM FOR PRIORITY

This application is a U.S. National Stage Application of PCT/EP2007/002140 filed on Mar. 12, 2007, claiming priority to European (EP) application 06447035.4 filed Mar. 13, 2006, the contents of both of which are incorporated herein by reference.

FIELD OF THE INVENTION

The invention relates generally to the field of cancer diagnosis, prognosis, treatment and prevention. More particularly, the present invention relates to methods of diagnosing, treating and preventing lung cancer. In particular, aspects of the invention are directed to methods of diagnosing, treating and preventing small cell lung cancers. Methods of using a nucleic acid and/or a protein, which are differentially expressed in tumor cells, and antibodies immunospecific for the protein, to treat, diagnose and/or prevent said cancers, are provided for by the present invention.

BACKGROUND TO THE INVENTION

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastases). Clinical data and molecular biologic studies indicate that cancer is a multistep process that begins with minor preneoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins & Angell, 1976, Basic Pathology, 2d Ed., W.B. Saunders Co., Philadelphia, pp. 68-79) The neoplastic lesion may evolve clonally and develop an increasing capacity for growth, metastasis, and heterogeneity, especially under conditions in which the neoplastic cells escape the host's immune surveillance (Roitt, I., Brostoff, J. and Kale, D., 1993, Immunology, 3rd ed., Mosby, St. Louis, pps. 17.1-17.12). The epidemiology of cancer in the United States is estimated at greater than 1,300,000 new cases and greater than 550,000 deaths (Jemal et al., 2003, CA Cancer J. Clin., 53, 5-26) estimated for 2003. Lung cancer is one of the most common cancers with an estimated 172,000 new cases projected for 2003 and 157,000 deaths in the US (Jemal et al., 2003, CA Cancer J. Clin., 53, 5-26). Lung carcinomas are typically classified as either small cell lung carcinomas (SCLC) or non-small cell lung carcinomas (NSCLC). SCLC comprises about 20% of all lung cancers with NSCLC comprising the remaining approximately 80%. NSCLC is further divided into adenocarcinoma (AC) (about 30-35% of all cases), squamous cell carcinoma (SCC) (about 30% of all cases) and large cell carcinoma (LCC) (about 10% of all cases). Additional NSCLC subtypes, not as clearly defined in the literature, include adenosquamous cell carcinoma (ASCC), and bronchioalveolar carcinoma (BAC).

Lung cancer is the leading cause of cancer deaths worldwide, and more specifically NSCLC accounts for approximately 80% of all disease cases (Cancer Facts and Figures, 2002, American Cancer Society, Atlanta, p. 11.). There are four major types of NSCLC, including adenocarcinoma, squamous cell carcinoma, bronchioalveolar carcinoma, and large cell carcinoma. Adenocarcinoma and squamous cell carcinoma are the most common types of NSCLC based on cellular morphology (Travis et al., 1996, Lung Cancer Principles and Practice, Lippincott-Raven, New York, pps. 361-395). Adenocarcinomas are characterized by a more peripheral location in the lung and often have a mutation in the K-ras oncogene (Gazdar et al., 1994, Anticancer Res. 14:261-267). Squamous cell carcinomas are typically more centrally located and frequently carry p53 gene mutations (Niklinska et al., 2001, Folia Histochem. Cytobiol. 39:147-148).

Lung carcinoma is the number one killer amongst cancer patients, for which no adequate treatment exists, corresponding to about one-fifth of all cancer deaths in Europe (IARC). The growing burden on the population is probably best illustrated from recent studies in the US, showing that between 1960 and 1990, deaths from lung cancer among woman increased over 400% in the period to exceed breast cancer deaths.

Currently no adequate treatment protocols for the different types of lung cancer exist. With conventional therapy, median survival for the subtype of SCLC is 15 months for limited-stage disease and 9 months for extensive-stage disease, whereas long-term survival is very low.

Major obstacles to the successful treatment and eradication of lung cancer are late diagnosis, highly metastatic behaviour, resistance to chemotherapy and the impossibility to surgically remove all cancer cells. In principle, cancer vaccines are a most promising approach for the treatment of cancer in general and lung cancer in particular. Major obstacles in the development of a successful vaccine are the lack of cancer specific antigens to be targeted and the lack of tools to evaluate immunotherapy based on such targets. An additional problem is the above cited heterogeneity of lung cancer.

In contrast to many other types of cancer, lung cancer treatment has not resulted in significant improvements in survival rates during the last decades, showing an overall 5-year survival of only 14% (Haura EB.2001, Cancer Control; 8: 326-336); Crawford J. (medscape, article 429347_1, published Mar. 01, 2002). To date the decision upon treatment protocols is especially guided by the subdivision into SCLC and NSCLC. Unlike the other types of lung cancer, SCLC is sensitive to chemotherapy. In about 75% of the cases of SCLC an initial response to chemotherapy can be noticed, with a clinically complete response in about 35% of all cases (Johnson D H, et al., 1987; Am J Med Sci 293: 377-389). Unfortunately, however, in most cases relapse occurs, resulting in a three year survival rate of only 5-10%, and a five-year survival rate of about 1% (Minna J D,et al. 1985, Cancer of the lung. In: Cancer. Principles and practice of oncology 2nd ed); Within SCLC a clinically relevant subdivision can be made between classic and variant SCLC. The variant-type of SCLC appears to be even less sensitive to chemotherapy and radiotherapy. As a result the median survival time of patients suffering from the variant-type of SCLC is significantly shorter than of those with a classic type of SCLC (Radice PA, et al. 1982, Cancer; 50: 2894-2902). Also for patients with a combined SCLC a poorer prognosis than for patients with classic SCLC is observed (Hirsch FR et al, 1983, Cancer; 52: 2144-2150). Approximately 75% to 80% of cases are of the NSCLC histology, and the majority of patients present with either locally advanced disease (stage III) or metastatic disease (stage IV). Importantly, patients undergoing curative surgical resection for apparent localized disease have survival rates ranging between 50% and 80%, implying the need for better systemic treatment to cure occult micrometastatic disease. In NSCLC treatment with chemotherapy is in general unsuccessful (Minna J D, et al. 1985, Cancer of the lung. In: Cancer. Principles and practice of oncology 2nd ed.). Therefore, with the exception of high cure rates for surgical treatment of truly localized disease, the prognosis for patients with NSCLC is grim (Mulshine J L,et al. 1986., J Clin Oncol; 4: 1704-1715). In a small subset of patients, however, a response to chemotherapy can be observed. In part, these cases might represent NSCLC in which SCLC-components occur since such a heterogeneous composition is quite common in lung cancer (see above) It may be obvious from these data that alternative treatment modalities for these patients are critical.

The main objective of the present invention is the development of a new model for the biology and antigenicity of lung cancer and developing a new concept for a lung cancer vaccination therapy. The approach will be directed towards target discovery—antigens specific for SCLC and NSCLC and immunization strategies.

A number of tumor-associated antigens have been identified in human lung cancers and are being used as targets for general lung cancer vaccines. These include the carcinoembryonic antigen (CEA), human epithelial mucin MUC-1, the cancer-testis antigen NY-ESO-1, and the ganglioside Fuc-GM1 (Haura E B. 2001, Cancer Control, 8: 326-336; www.medscape.com/viewarticle/409059). Vaccination of tumor patients with inactivated tumor cells has been tried decades ago with not much success. The intra-tumoral injection of heat-killed *Mycobacteria* into SCLC lesions as an adjuvant with autologous tumor cells has led to some success.

NSCLC can evoke specific humoral and cellular antitumor immune responses in some patients (Salgia R, et al. 2003; J clin Oncol; 21:624-630.). Serology-based cloning strategies have identified multiple tumor-associated antigens, including eIF4G, aldolase, annexin XI, Rip-1, and NY-LU-12. Humoral responses to autologous lung cancer cells may be associated with prolonged survival. T-cell-based cloning strategies similarly have revealed diverse targets in NSCLC, including Her2/neu, SART-1, SART-2, KIAA0156, ART-1, ART-4, cyclophilin B, mutated elongation factor 2, malic enzyme, and alpha-actinin-4. The development of cytotoxic T-lymphocyte responses to NSCLC may also be correlated with prolonged survival.

In clinical practice, accurate diagnosis of various subtypes of cancer is important because treatment options, prognosis, and the likelihood of therapeutic response all vary broadly depending on the diagnosis. Accurate prognosis, or determination of distant metastasis-free survival could allow an oncologist to tailor the administration of adjuvant chemotherapy, with patients having poorer prognoses being given more aggressive treatment. Furthermore, accurate prediction of poor prognosis would greatly impact clinical trials for new lung cancer therapies, because potential study patients could then be stratified according to prognosis. Trials could be limited to patients having poor prognosis, in turn making it easier to discern if an experimental therapy is efficacious. To date, no set of satisfactory predictors for prognosis based on the clinical information alone has been identified.

It would, therefore, be beneficial to provide specific methods and reagents for the diagnosis, staging, prognosis, monitoring and treatment of cancer, including lung cancer. It would also be beneficial to provide methods that identify individuals with a predisposition for the onset of lung cancer, and other types of cancer, and hence are appropriate subjects for preventive therapy.

SUMMARY OF THE INVENTION

Using differential expression methods the present inventors identified and characterized the NCAM-180 and variants thereof, as a gene whose expression is associated with lung cancer and other types of cancer. This discovery by the present inventors has made possible the use of NCAM-180 molecules and variants thereof for the treatment, prevention and diagnosis of cancers, including but not limited to lung cancer, in particular also in the treatment, prevention and diagnosis of neuronal and neuroendocrine cancers.

The novel NCAM-180 has an upregulated expression pattern in cancer tissues and cell lines, e.g., lung cancer tissues and cell lines are shown and described. Also shown and described is Exon18_MUM a fragment of NCAM-180 that retains at least one functional characteristic of the full length, wild type NCAM-180 gene. Methods of using the gene, gene products, and antagonists or agonists of the gene or gene products (NCAM-180 and variants thereof, cDNA, RNA, and/or protein) as targets for diagnosis, drug screening and therapies for cancer are also shown and described. Also disclosed is the use of the genes or gene products or derivatives thereof as vaccines against cancer. In one embodiment, methods are provided for using an NCAM-180 protein (such as SEQ ID No. 4), fragments thereof, in particular Exon18_MUM (such as SEQ ID NOs: 2 and 6), and variants thereof, or nucleic acids that encode said proteins for the treatment, prevention and diagnosis of lung cancer.

Isolated nucleotide sequences of NCAM-180 gene cDNA or variants thereof are provided. Specifically, isolated cDNA sequences of human NCAM-180 and the Exon18_MUM fragments thereof (SEQ ID NOs: 1, 3 and 5) are provided herein. Also provided are isolated amino acid sequences encoded by SEQ ID NOs: 1, 3 and 5 which are denoted SEQ ID NOs: 2, 4 and 6.

The present invention further relates to methods for the diagnostic evaluation and prognosis of cancer in a subject animal. Preferably the subject is a mammal, more preferably the subject is a human. In a preferred embodiment the invention relates to methods for diagnostic evaluation and prognosis of lung cancer. For example, nucleic acid molecules of the invention can be used as diagnostic hybridization probes or as primers for diagnostic PCR analysis for detection of abnormal expression of an NCAM-180 gene.

Antibodies or other binding partners to NCAM-180 or variants thereof can be used in a diagnostic test to detect the presence of an NCAM-180 product in body fluids, cells or in tissue biopsy. In specific embodiments, measurement of serum or cellular NCAM-180 and variants thereof can be made to detect or type lung cancer, e.g., adenocarcinoma, squamous cell carcinoma, bronchioalveolar carcinoma, or large cell carcinoma; in particular to detect or type SCLC.

Further, methods are presented for the treatment of cancer, including lung cancer. Such methods comprise the administration of compositions that are capable of modulating the level of NCAM-180 and variants thereof, including modulation of NCAM-180 gene expression and/or the level of an NCAM-180 gene product activity in a subject. The subject can be any animal, preferably a mammal, more preferably a human.

The invention also provides methods for preventing cancer wherein NCAM-180 or variants thereof, in particular Exon18_MUM or fragments thereof that are capable of inducing a humoral or a cellular immune response in a mammal, is administered to a subject in an amount effective to elicit an immune response in the subject. The Exon18_MUM fragments are further characterized in that they comprise from 5 to 30 amino acids, in particular from 9 to 15 amino acids and comprise an epitope selected from PAASNLSSSVLAN (AA101-113 of SEQ ID NO:2), VLSPSAPAGVG (AA 117-127 of SEQ ID NO:2), LAAAAAPATEAPQ (AA 153-165 of SEQ ID NO:2), KGPDPEPTQPGA (AA 174-185 of SEQ ID NO:2) and DFKMDEGNFK (AA 216-225 of SEQ ID NO:2).

The subject may be any animal, preferably a mammal, more preferably a human. The invention also provides methods for treating or preventing cancer by administering a nucleic acid sequence encoding an NCAM-180 protein or a variant, in particular encoding for Exon18_MUM or fragments thereof that are capable of inducing a humoral or a cellular immune response in a mammal, thereof to a subject such that expression of the NCAM-180 protein or variant results in the production of these polypeptides in an amount effective to elicit an immune response. The immune response may be humoral, cellular, or a combination of both. In a preferred embodiment the invention provides a method of immunizing to confer protection against the onset of lung cancer.

The invention also provides methods for treating cancer by providing therapeutic amounts of an anti-sense nucleic acid molecule. An anti-sense molecule is a nucleic acid molecule that is a complement of all or a part of an NCAM-180 gene sequence and which, therefore, can hybridize to the NCAM-180 gene and variants thereof, in particular to Exon18_MUM, a fragment of NCAM-180. Accordingly, hybridization of the anti-sense molecule can reduce or inhibit expression of NCAM-180. In a preferred embodiment the method is used to treat lung cancer.

The invention also includes a kit for assessing whether a patient is afflicted with lung cancer or other types of cancer. This kit comprises reagents for assessing expression levels of NCAM-180 or a variant, including fragments thereof such as Exon18_MUM or fragments thereof that are capable of inducing a humoral or a cellular immune response in a mammal. In another aspect, the kit comprises an antibody, wherein the antibody binds specifically with a protein corresponding to NCAM-180 and variants thereof, in particular Exon18_MUM or fragments thereof that are capable of inducing a humoral or a cellular immune response in a mammal. The kit may also comprise a plurality of antibodies, wherein the plurality binds specifically with different epitopes of an NCAM-180 and variants thereof, in particular with Exon18_MUM fragments that comprise from 5 to 30 amino acids, in particular from 9 to 15 amino acids and comprise an epitope selected from PAASNLSSSVLAN (AA101-113 of SEQ ID NO:2), VLSPSAPAGVG (AA 117-127 of SEQ ID NO:2), LAAAAAPATEAPQ (AA 153-165 of SEQ ID NO:2), KGPDPEPTQPGA (AA 174-185 of SEQ ID NO:2) and DFKMDEGNFK (AA 216-225 of SEQ ID NO:2).

In an alternative embodiment, the kit comprises a nucleic acid (e.g., oligonucleotide) probe. The probe binds specifically to a transcribed polynucleotide corresponding to an NCAM-180 gene product and variants thereof. The kit may also comprise a plurality of probes, wherein each of the probes binds specifically to a transcribed polynucleotide corresponding to a different region of the mRNA sequence transcribed from the NCAM-180 gene and variants thereof, in particular to the nucleic acid sequence encoding for Exon18_MUM, a fragment of NCAM-180. In a more particular embodiment probes consist essentially of 15 to 50, 18 to 35, to 24, 18 to 30, 18 to 21 or 21 to 24 nucleotides of a sequence encoding a polypeptide of the invention or its complement. In an even further embodiment, kits for diagnostic use, including primers for use in PCR that can amplify an NCAM-180 cDNA and variants thereof, including the corresponding cDNA and/or genes and a standard amount of the NCAM-180 cDNA are also provided.

Accordingly, the present invention provides a method of diagnosing cancer in a subject comprising detecting or measuring an NCAM-180 product or a variant thereof, including fragments thereof such as Exon18_MUM, in a sample derived from said subject, wherein said NCAM-180 product is (a) an RNA corresponding to one of SEQ ID NOs: 1, 3 or 5, or a nucleic acid derived therefrom; (b) a protein comprising one of SEQ ID NOs: 2, 4 or 6; (c) a nucleic acid comprising a sequence hybridizable to one of SEQ ID NOs: 1, 3 or 5, or a complement thereof under conditions of high stringency, or a protein comprising a sequence encoded by said hybridizable sequence; (d) a nucleic acid at least 90% homologous to one of SEQ ID NOs: 1, 3 or 5, or a complement thereof as determined using the NBLAST algorithm, or a protein encoded thereby, in which elevated levels of an NCAM-180 product and variants thereof, compared to a non-cancerous sample or a pre-determined standard value for a non-cancerous sample, indicates the presence of a cancer in the subject.

In one embodiment of the foregoing diagnostic method, the subject is a human. In another embodiment, the cancer is lung cancer. In yet other embodiments, the sample is a tissue sample, a plurality of cells, or a bodily fluid.

The present invention further provides methods for treating cancer in a subject, comprising administering to the subject an amount of a compound which reduces the level and/or antagonizes the activity of an NCAM-180 product and variants thereof, including fragments such as Exon18_MUM and others as defined hereinbefore, wherein said NCAM-180 product is (a) an RNA corresponding to one of SEQ ID NOs: 1, 3 or 5, or a nucleic acid derived therefrom; (b) a protein comprising one of SEQ ID NOs: 2, 4 or 6; (c) a nucleic acid comprising a sequence hybridizable to one of SEQ ID NOs: 1, 3 or 5, or a complement thereof under conditions of high stringency, or a protein comprising a sequence encoded by said hybridizable sequence; (d) a nucleic acid at least 90% homologous to one of SEQ ID NOs: 1, 3 or 5, or a complement thereof as determined using the NBLAST algorithm, or a protein encoded thereby. In one embodiment, a gene product whose expression is being decreased is a protein encoded by a nucleic acid comprising a nucleotide sequence with at least 90% sequence identity to one of SEQ ID NOs: 1, 3 or 5. In another embodiment, the compound decreases expression of an RNA corresponding to one of SEQ ID NOs: 1, 3 or 5. The antagonist can be (i) a protein; (ii) a peptide; (iii) an organic molecule with a molecular weight of less than 2000 daltons; (iv) an inorganic molecule with a molecular weight of less than 2000 daltons; (v) an antisense oligonucleotide molecule that binds to said RNA and inhibits translation of said RNA; (vi) a ribozyme molecule that targets said RNA and inhibits translation of said RNA; (vii) an antibody that specifically or selectively binds to an NCAM-180 product and variants thereof as defined herein; (viii) a double stranded oligonucleotide that forms a triple helix with a promoter of an NCAM-180 gene and variants thereof, wherein said NCAM-180 gene is a nucleic acid at least 80% homologous to one of SEQ ID NOs: 1, 3 or 5, or a complement thereof as determined using the NBLAST algorithm; or (ix) a double stranded oligonucleotide that forms a triple helix with a promoter of an L gene, wherein said NCAM-180 gene is a nucleic acid at least 80% homologous to one of SEQ ID NOs: 1, 3 or 5, or a complement thereof as determined using the NBLAST algorithm. Wherein the compound is an NCAM-180 antagonist antibody, the antibody immunospecifically binds to a protein comprising an amino acid sequence of one of SEQ ID NOs: 2, 4 or 6 and thereby reduces or inhibits an activity of a protein according to the invention.

The present invention further provides methods of vaccinating a subject against cancer comprising administering to the subject a molecule that elicits an immune response to an NCAM-180 gene product, wherein said NCAM-180 gene product is (a) an RNA corresponding to one of SEQ ID NOs: 1 or 3, or a nucleic acid derived therefrom; (b) a protein comprising one of SEQ ID NOs: 2 or 6; (c) a nucleic acid comprising a sequence hybridizable to one of SEQ ID NOs: 1 or 3, or a complement thereof under conditions of high stringency, or a protein comprising a sequence encoded by said hybridizable sequence; (d) a nucleic acid at least 90% homologous to one of SEQ ID NOs: 1 or 3, or a complement thereof as determined using the NBLAST algorithm, or a protein encoded thereby. In one embodiment, the immune response is a cellular immune response. In another embodiment, the immune response is a humoral immune response. In yet another embodiment, the immune response is both a cellular and a humoral immune response.

The present invention yet further provides a vaccine formulation for preventing or delaying the onset of cancer comprising (I) an immunogenic amount of NCAM-180 product, wherein said NCAM-180 product is: (a) an RNA corresponding to one of SEQ ID NOs: 1, 3 or 5, or a nucleic acid derived therefrom; (b) a protein comprising one of SEQ ID NOs: 2, 4 or 6 or a fragment of one of SEQ ID NOs: 2, 4 or 6, wherein said fragment is capable of inducing a humoral or cellular response in a mammal, in particular a cytotoxic T lymphocyte (CTL) response in a mammal; (c) a nucleic acid comprising a sequence hybridizable to one of SEQ ID NOs: 1, 3 or 5, or a complement thereof under conditions of high stringency, or a protein comprising a sequence encoded by said hybridizable sequence; (d) a nucleic acid at least 90% homologous to one of SEQ ID NOs: 1, 3 or 5, or a complement thereof as determined using the NBLAST algorithm, or a protein encoded thereby; and (II) a pharmaceutically acceptable excipient. In a particular embodiment the fragment capable of inducing a humoral or cellular response in a mammal comprises from 5 to 30 amino acids of any one of SEQ ID NO. 2, 4 or 6, in particular from 9 to 15 amino acids and comprise an epitope selected from PAASNLSSSVLAN (AA101-113 of SEQ ID NO:2), VLSPSAPAGVG (AA 117-127 of SEQ ID NO:2), LAAAAAPATEAPQ (AA 153-165 of SEQ ID NO:2), KGPDPEPTQPGA (AA 174-185 of SEQ ID NO:2) and DFKMDEGNFK (AA 216-225 of SEQ ID NO:2).

The present invention yet further provides a pharmaceutical composition comprising an antibody that specifically or selectively binds to a protein consisting essentially of one of SEQ ID NOs: 2, 4 or 6; and a pharmaceutically acceptable carrier. In an even further embodiment the pharmaceutical composition comprises an antibody that specifically or selectively binds to a fragment of one of SEQ ID NOs: 2, 4 or 6, wherein said fragment comprises from 5 to 30 amino acids, more in particular from 9 to 15 amino acids of any one of SEQ ID NO. 2, 4 or 6.

The present invention further provides host cells comprising nucleic acids encoding the polypeptides of the invention operably linked to a promoter, and methods of expressing such polypeptides and variants thereto by culturing the host cells under conditions in which the nucleic acid molecule is expressed. It is accordingly an object of the present invention to provide the use of said host cells in methods for treating or preventing cancer in a subject, comprising administering to the subject (I) an amount of host cells expressing an immunogenic amount of an NCAM-180 product, wherein said NCAM-180 product is: (a) an RNA corresponding to one of SEQ ID NOs: 1, 3 or 5, or a nucleic acid derived therefrom; (b) a protein comprising one of SEQ ID NOs: 2, 4 or 6, or fragments of SEQ ID NOs: 2, 4 or 6, wherein said fragments are capable of inducing a humoral or cellular response in a mammal, in particular a CTL response as defined hereinbefore; (c) a nucleic acid comprising a sequence hybridizable to one of SEQ ID NOs: 1, 3 or 5, or a complement thereof under conditions of high stringency, or a protein comprising a sequence encoded by said hybridizable sequence; (d) a nucleic acid at least 90% homologous to one of SEQ ID NOs: 1, 3 or 5, or a complement thereof as determined using the NBLAST algorithm, or a protein encoded thereby; and optionally (II) a pharmaceutically acceptable excipient.

It is accordingly an object of the present invention to provide a method of vaccinating a subject against cancer, said method comprising administering to the subject an amount of host cells expressing an immunogenic amount of an NCAM-180 product, wherein said NCAM-180 product is as defined hereinbefore, including the Exon_18MUM fragments and the fragments that are capable to induce a CTL response in a mammalian cell; and optionally (II) a pharmaceutically acceptable excipient. In a particular embodiment the NCAM-180 product is selected from the group consisting of: (a) an RNA corresponding to one of SEQ ID NOs: 1, 3 or 5, or a nucleic acid derived therefrom; (b) a protein comprising one of SEQ ID NOs: 2, 4 or 6; (c) a nucleic acid comprising a sequence hybridizable to one of SEQ ID NOs: 1, 3 or 5, or a complement thereof under conditions of high stringency, or a protein comprising a sequence encoded by said hybridizable sequence; (d) a nucleic acid at least 90% homologous to one of SEQ ID NOs: 1, 3 or 5, or a complement thereof as determined using the NBLAST algorithm, or a protein encoded thereby. The subject can be any animal, preferably a mammal, more preferably a human.

These and other aspects of the invention are described herein in more detail.

Description of Sequences.

SEQ ID NO:1 is the nucleotide sequence for human Exon18_MUM.

SEQ ID NO:2 is the amino acid sequence for human Exon18_MUM.

SEQ ID NO:3 is the nucleotide sequence for human NCAM-180.

SEQ ID NO:4 is the amino acid sequence for human NCAM-180.

SEQ ID NO:5 is the nucleotide sequence for a fragment of human Exon18_MUM.

SEQ ID NO:6 is the amino acid sequence for the fragment of human Exon18_MUM encoded by SEQ ID NO:5

BRIEF DESCRIPTION OF THE DRAWINGS

FIG. 4: CTL response as measured after in vitro re-stimulation with a Exon18_MUM overlapping 9-mer peptide pool. Mice were immunized with Exon18_MUM protein and/or DNA. Spleens were isolated, spleen cells harvested and seeded in 96 well culture plates. Subsequently, in vitro re-stimulation was performed with an Exon18_MUM overlapping 9-mer, peptide pool. The number of IFN-γ secreting cells per $10^5$ CD8+ T-cells was measured using flowcytometry. IPP=irrelevant peptide=re-stimulation performed with peptides not related to the NCAM Exon18_MUM protein region.

For each group immunization was done twice. Reagents used for prime are represented before the /, reagents used for boost are represented after the /. The djuvant used is Abisco-100.
A: PBS/PBS
B: Adjuvant/Adjuvant
C: Exon18_MUM protein in Adjuvant/Exon18_MUM protein in Adjuvant
D: Exon18_MUM protein/Exon18_MUM protein
E: Empty pCI vector/empty pCI vector
F: Exon18_MUM pCI/Exon18_MUM pCI
G: Exon18_MUM pCI/Exon18_MUM protein in Adjuvant

FIG. 6: A In Exon18_MUM DNA immunized mice cytotoxic T-cell responses were measured. Mice spleen cells were in vitro re-stimulated with individual 9-mer peptides. The number of intracellular IFN-γ containing CD8 positive T-cells was measured using a FACS based read-out. B predicted score $H-2^{db}$ haplotype.

FIG. 7: Humoral response as measured by NCAM Exon18_MUM protein ELISA. Mice were immunized with truncated Exon18_MUM protein and/or truncated Exon18_MUM DNA. Mice were bled, serum was isolated and diluted 1/200 with buffer. ELISA plates were coated with Exon18_MUM protein, and detection of bound antibody was performed using an HRP conjugated anti-mouse IgG. OD was measured at 450 nm.

FIG. 8: Humoral response as measured by NCAM Exon18_MUM protein ELISA. Mice were immunized with truncated Exon18_MUM protein. Mice (50 in total, 5 in each group) were bled, serum was isolated and diluted (range 1/50-1/135,000) with buffer. ELISA plates were coated with respectively full-length Exon18_MUM protein A and truncated Exon18_MUM protein B. Detection of bound antibody was performed using an HRP conjugated anti-mouse IgG. OD was measured at 450 nm.

DETAILED DESCRIPTION OF THE INVENTION

Figure 1:
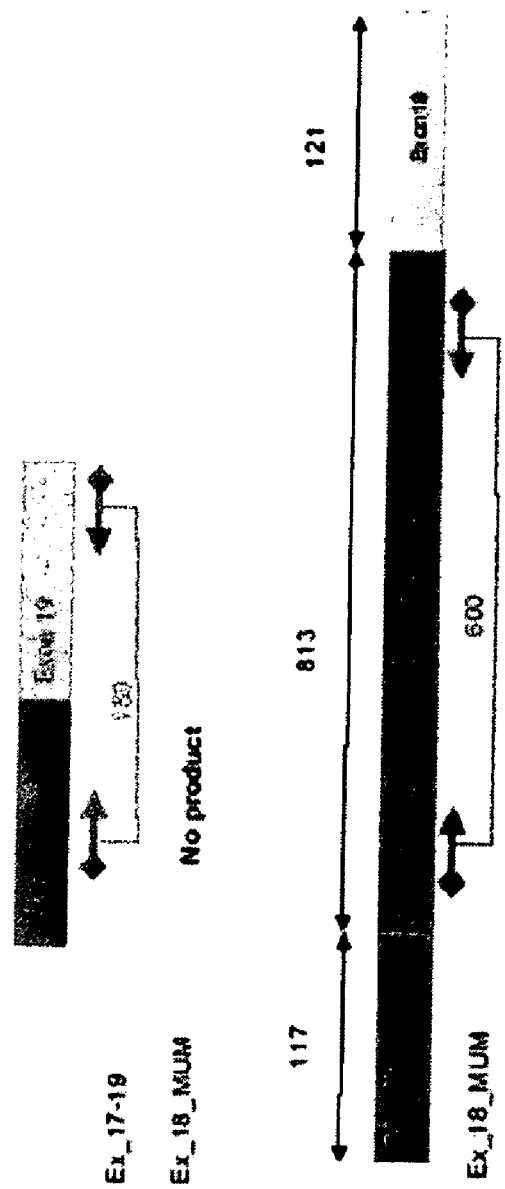
FIG. 1 Schematic representation of the principle of the differential expression PCR. For primer set A, the forward primer was designed in exon 17, the reverse primer in exon 19. For primer set B, the forward as well as the reverse primer was designed in Exon18_MUM. PCR amplification of cells expressing NCAM-140 resulted in a 180 bp PCR product with primerset A, and no amplicon with primerset B. Cells expressing NCAM-180 produce a 600 bp PCR amplicon with primerset B. Cells expressing both NCAM-140 and NCAM-180 produce PCR products with both primersets.

The following definitions are set forth to clarify aspects of the invention: SPECIFIC OR SELECTIVE: a nucleic acid used in a reaction, such as a probe used in a hybridization reaction, a primer used in a PCR, or a nucleic acid present in a pharmaceutical preparation, is referred to as "selective" if it hybridizes or reacts with the intended target more frequently, more rapidly, or with greater duration than it does with alternative substances. Similarly, a polypeptide is referred to as "selective" if it binds an intended target, such as a ligand, hapten, substrate, antibody, or other polypeptide more frequently, more rapidly, or with greater duration than it does to alternative substances. An antibody is referred to as "selective" if it binds via at least one antigen recognition site to the intended target more frequently, more rapidly, or with greater duration than it does to alternative substances. A marker is selective to a particular cell or tissue type if it is expressed predominantly in or on that cell or tissue type, particularly with respect to a biological sample of interest.

VARIANT (S): A variant (v) of polynucleotides or polypeptides, as the term is used herein, are polynucleotides or polypeptides that are different from a reference polynucleotide or polypeptide, respectively. Variant polynucleotides are generally limited so that the nucleotide sequence of the reference and the variant are closely related overall and, in many regions, identical. Changes in the nucleotide sequence of the variant may be silent. That is, they may not alter the amino acid sequence encoded by the polynucleotide. Where alterations are limited to silent changes of this type a variant will encode a polypeptide with the same amino acid sequence as the reference. Alternatively, changes in the nucleotide sequence of the variant may alter the amino acid sequence of a polypeptide encoded by the reference polynucleotide. Such nucleotide changes may result in amino acid substitutions, additions, deletions, fusions, and truncations in the polypeptide encoded by the reference sequence. Variant polypeptides are generally limited so that the sequences of the reference and the variant are closely similar overall and, in many regions, identical. For example, a variant and reference polypeptide may differ in amino acid sequence by one or more substitutions, additions, deletions, fusions, and truncations, which may be present or absent in any combination.

CORRESPOND OR CORRESPONDING: Between nucleic acids, "corresponding" means homologous to or complementary to a particular sequence or portion of the sequence of a nucleic acid. As between nucleic acids and polypeptides, "corresponding" refers to amino acids of a peptide in an order derived from the sequence or portion of the sequence of a nucleic acid or its complement. As between polypeptides (or peptides and polypeptides), "corresponding" refers to amino acids of a first polypeptide (or peptide) in an order derived from the sequence or portion of the sequence of a second polypeptide.

NCAM-180 GENE: As used herein, unless otherwise indicated, refers to the novel NCAM splice variant discovered herein to be up-regulated in certain cancers (e.g., lung cancer) and subsets thereof.

NCAM-180 PRODUCT or NCAM-180 GENE PRODUCT: As used herein, unless otherwise indicated, an NCAM-180 product is: an RNA corresponding to one of SEQ ID NOs: 1, 3 or 5, or a nucleic acid derived therefrom; a protein comprising one of SEQ ID NOs: 2, 4 or 6; a nucleic acid comprising a sequence hybridizable to one of SEQ ID NOs: 1, 3 or 5 or a complement thereof under conditions of high stringency, or a protein comprising a sequence encoded by said hybridizable sequence; a nucleic acid at least 90% homologous to one of SEQ ID NOs: 1, 3 or 5 or a complement thereof as determined using the NBLAST algorithm; a nucleic acid at least 90% homologous to one of SEQ ID NO.: 1 or a fragment or derivative of any of the foregoing proteins or nucleic acids, in particular Exon18_MUM a fragment of NCAM-180, hereinafter also referred to as MUM protein or NCAM-MUM, encoded by any of SEQ ID NOs.:3 or SEQ ID NO.: 5. In an even further embodiment a fragment of said NCAM-180 or Exon18_MUM is characterized in that it comprises from 5 to 30 amino acids, more in particular from 9 to 15 amino acids and comprises an epitope selected from PAASNLSSSVLAN (AA101-113 of SEQ ID NO:2), VLSPSAPAGVG (AA 117-127 of SEQ ID NO:2), LAAAAAPATEAPQ (AA 153-165 of SEQ ID NO:2), KGPDPEPTQPGA (AA 174-185 of SEQ ID NO:2) and DFKMDEGNFK (AA 216-225 of SEQ ID NO:2).

CONTROL ELEMENTS: As used herein refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements is required so long as the selected coding sequence is capable of being replicated, transcribed and translated in an appropriate host cell.

PROMOTER REGION: Is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

OPERABLY LINKED: As used herein refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof.

EXOGENOUS: As used herein the term exogenous refers to that which is derived or originated externally. When used in the context of exogenous expression of a gene or protein, the term refers to a gene or protein that is being expressed in a cell or tissue that does not normally express the gene or protein. When used in the context of nucleic acid sequences, for example, the term may also be used to refer to an association of two or more nucleic acid sequences that have been operably linked, but are not normally operably linked in a native state.

TO TREAT A CANCER OR A TUMOR: As used herein, the phrase "to treat a cancer or a tumor" or "treating a cancer or a tumor" in a mammal means one or more of alleviating a symptom of, correcting an underlying molecular or physiological disorder of, or reducing the frequency or severity of a pathological or deleterious physiological consequence of a cancer or a tumor in a mammal. By way of example, and not by limitation, the deleterious physiological consequences of a cancer or a tumor can include uncontrolled proliferation, metastasis and invasion of other tissues, and suppression of an immune response.

IMMUNOLOGICALLY SPECIFIC: With respect to antibodies of the invention, the term "immunologically specific" refers to antibodies that bind to one or more epitopes of a protein of interest (e.g., Exon18_MUM protein), but which do not substantially recognize and bind other molecules in a sample containing a mixed population of antigenic biological molecules.

CONSISTING ESSENTIALLY OF: The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence. Such an amino acid sequence exhibits 80% sequence homology or greater, i.e. 85%, 90%, 95%, 97%, 98%, 99% or more to that of the given SEQ ID NO:. In particular such an amino acid sequence exhibits 80% sequence identity or greater, i.e. 85%, 90%, 95%, 97%, 98%, 99% or more to that of the given SEQ ID NO:.

ANTAGONIST: As used herein, a compound capable of reducing the level and/or activity of NCAM-180 or a variant thereof may be referred to herein as an NCAM-180 antagonist.

AGONIST: As used herein, a compound capable of increasing the level and/or activity of NCAM-180 or a variant thereof may be referred to herein as an NCAM-180 agonist.

NCAM-180 ACTIVITY: As used herein, the terms "NCAM-180 activity", "NCAM-180 product activity", or "NCAM-180 mediated activity" refer to an activity associated with the expression of NCAM-180 and/or an NCAM-180 product. Such activities include, but are not limited to changes in cellular proliferation, cellular motility, cellular differentiation, and/or cellular adhesion associated with changes in NCAM-180 expression levels. As used herein the terms "elevated", "over-expressed", "up-regulated", or "increased" refer to an approximately two-fold or greater increase in the expression of NCAM-180 transcript and/or protein as compared to that of a control tissue, which expresses a baseline level of NCAM-180.

Nucleic Acid

Nucleic acid as used in the methods of the present invention includes DNA (including both genomic and cDNA) and RNA. Where nucleic acid according to the invention includes RNA, reference to the sequences shown in the accompanying listings should be construed as reference to the RNA equivalent, with U substituted for T.

Nucleic acid of the invention may be single or double stranded. Single stranded nucleic acids of the invention include anti-sense nucleic acids. Thus it will be understood that reference to SEQ ID NO:1 or sequences comprising SEQ ID NO:1 or fragments thereof include complementary sequences unless the context is clearly to the contrary. The same applies to SEQ ID NOs:3 or 5.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression.

Nucleic acid may be wholly or partially synthetic and may include genomic DNA, cDNA or RNA.

The invention also provides nucleic acids that are fragments of the nucleic acids encoding a polypeptide of the invention. In one aspect, the invention provides nucleic acids primers or probes which consist essentially of from 15 to 50, for example from 15 to 35, 18 to 35, 15 to 24, 18 to 30, 18 to 21 or 21 to 24 nucleotides of a sequence encoding a polypeptide of the invention or its complement.

The term "consist essentially of" refers to nucleic acids which do not include any additional 5' or 3' nucleic acid sequences. In a further aspect of the invention, nucleic acids of the invention which consist essentially of from 15 to 30 nucleotides as defined above may however be linked at the 3' but preferably 5' end to short (e.g from 4 to 15, such as from 4 to 10 nucleotides) additional sequences to which they are not naturally linked. Such additional sequences are preferably linkers which comprise a restriction enzyme recognition site to facilitate cloning when the nucleic acid of the invention is used for example as a PCR primer.

Primers and probes of the invention are desirably capable of selectively hybridising to nucleic acids encoding the polypeptides of the invention. By "selective", it is meant selective with respect to sequences encoding other purine receptors and in particular with respect to receptors other than adenine receptors. The ability of the sequence to hybridize selectively may be determined by experiment or calculated.

For example, one way to calculate Tm of a primer is by reference to the formula for calculating the Tm of primers to a homologous target sequence. This formula is $Tm(° C.)=2(A+T)+4(G+C)-5$. This will provide the Tm under conditions of 3×SSC and 0.1% SDS (where SSC is 0.15M NaCl, 0.015M sodium citrate, pH 7). This formula is generally suitable for primers of up to about 50 nucleotides in length. In the present invention, this formula may be used as an algorithm to calculate a nominal Tm of a primer for a specified sequence derived from a sequence encoding a polypeptide of the invention. The Tm may be compared to a calculated Tm for GPCR sequences of humans and rats, based upon the maximum number of matches to any part of these other sequences.

Suitable conditions for a primer to hybridize to a target sequence may also be measured experimentally. Suitable experimental conditions comprise hybridising a candidate primer to both nucleic acid encoding a polypeptide of the invention and nucleic acid encoding other adenine receptors on a solid support under low stringency hybridising conditions (e.g. 6×SSC at 55° C.), washing at reduced SSC and/or higher temperature, for example at 0.2×SSC at 45° C., and increasing the hybridisation temperature incrementally to determine hybridisation conditions which allow the primer to hybridize to nucleic acid encoding a polypeptide of the invention but not other purine receptor encoding nucleic acids.

Nucleic acids of the invention, particularly probes, may carry a revealing label. Suitable labels include radioisotopes such as $^{32}P$ or $^{35}S$, fluorescent labels, enzyme labels, or other protein labels such as biotin. Such labels may be added to polynucleotides or primers of the invention and may be detected using by techniques known per se.

Primers of the present invention may be comprised of synthetic nucleic acids, such as those with modified backbone structures intended to improve stability of the nucleic acid in a cell. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or lifespan of polynucleotides of the invention.

Also included within the scope of the invention are antisense sequences based on the nucleic acid sequences described herein, preferably in the form of oligonucleotides, particularly stabilized oligonucleotides, or ribozymes.

Antisense oligonucleotides may be designed to hybridize to the complementary sequence of nucleic acid, pre-mRNA or mature mRNA, interfering with the production of polypeptide encoded by a given target DNA sequence, so that its expression is reduced or prevented altogether. Ribozymes will be designed to cleave mRNA encoded by an NCAM-180 encoding nucleic acid sequence of the invention, desirably at a target sequence specific to the NCAM-180 gene products as defined hereinbefore, including sequences according to SEQ ID Nos.: 1, 3 or 5. The construction of antisense sequences and their use is described in Peyman and Ulman, Chemical Reviews, 90:543-584, (1990), Crooke, Ann. Rev. Pharmacol. Toxicol.; 32:329-376, (1992), and Zamecnik and Stephenson, P.N.A.S, 75:280-284, (1974). The construction of ribozymes and their use is described in for instance Gibson and Shillitoe, Molecular Biotechnology 7(2): 125-137, (1997).

The cDNA sequence of the NCAM-180 of the invention may be cloned using standard PCR (polymerase chain reaction) cloning techniques. This involves making a pair of primers to 5' and 3' ends on opposite strands of SEQ ID NO:1, bringing the primers into contact with mRNA or cDNA obtained from a mammalian cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. The same applies to SEQ ID NOs:3 or 5.

Polynucleotides which are not 100% homologous to the sequence of SEQ ID NOs: 1, 3 or 5 but which encode either SEQ ID NOs:2, 4 or 6 or other polypeptides of the invention can be obtained in a number of ways.

For example, site directed mutagenesis of the sequence of SEQ ID NO: 1, 3 or 5 may be performed. This is useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes which are required to provide, for example, conservative substitutions.

Nucleic acids of the invention may comprise additional sequences at the 5' or 3' end. For example, synthetic or natural 5' leader sequences may be attached to the nucleic acid encoding polypeptides of the invention. The additional sequences may also include 5' or 3' untranslated regions required for the transcription of nucleic acid of the invention in particular host cells.

In addition, other animal, particularly mammalian (e.g. monkey or rabbits), more particularly primate including monkey, homologues of NCAM-180 may be obtained and used in the methods of the present invention. Such sequences may be obtained by making or obtaining cDNA libraries made from dividing cells or tissues or genomic DNA libraries from other animal species, and probing such libraries with probes comprising all or part of SEQ ID NO:1, 3 or 5 under conditions of medium to high stringency (for example 0.03M sodium chloride and 0.03M sodium citrate at from about 50 C. to about 60 C).

The present invention further extends to an isolated DNA sequence comprising sequences encoding a polypeptide of the invention but in which the encoding sequences are divided up into two or more (preferably no more than five, e.g. four or three) exons. Such exon sequences may be natural and obtained from genomic clones, or synthetic. Exon sequences may be used in the construction of mini-gene sequences which comprise nucleic acid encoding polypeptides of the invention which sequences are interrupted by one or more exon sequences.

Mini-genes may also be constructed using heterologous exons, derived from any eukaryotic source.

Polypeptides.

Isolated polypeptides used in the methods of the present invention will be those as defined above in isolated form, free or substantially free of material with which it is naturally associated such as other polypeptides with which it is found in the cell. The polypeptides may of course be formulated with diluents or adjuvants and still for practical purposes be isolated—for example the polypeptides will normally be mixed with gelatin or other carriers if used to coat microtitre plates for use in immunoassays. The polypeptides may be glycosylated, either naturally or by systems of heterologous eukaryotic cells, or they may be (for example if produced by expression in a prokaryotic cell) unglycosylated. Polypeptides may be phosphorylated and/or acetylated.

A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

Polypeptides of the invention may be modified for example by the addition of histidine residues to assist their purification or by the addition of a signal sequence to promote their secretion from a cell.

In one embodiment, the present invention relates to fusion proteins, comprising the NCAM-180 polypeptides, fragments or derivatives of the present invention and a heterologous protein or part of a protein acting as a fusion partner. The proteins of the present invention and the fusion partner may be chemically conjugated, but are preferably expressed as recombinant fusion proteins in a heterologous expression system. The fusion partner can either be an immunological fusion partner that may assist in providing T helper epitopes, or act as an expression enhancer. Thus the immunological fusion protein may act through a bystander helper effect linked to the secretion of activation signals by a large number of T-cells specific to the foreign protein or peptide, thereby enhancing the induction of immunity to the NCAM-180 protein. Preferably the heterologous partner is selected to be recognized by T-cells in a majority of humans. The expression enhancer will allow increased levels of NCAM-180 protein to be produced as compared to the native recombinant protein and include chaperones that assist folding of nascent proteins, in particular the HSP70 or HSP60 families and the C-terminal domains of said heat shock proteins which are known to interact with substrate proteins and immunogenic peptides. Preferably the fusion partner will be both an immunological fusion protein and an expression enhancer partner. Accordingly, the present invention provides fusion proteins of the NCAM-180 proteins, fragments or derivatives according to the invention, linked to a fusion partner. In a further embodiment the fusion partner is selected from the group consisting of the non-structural protein from influenza virus, NS1 (hemagglutinin) or the C-terminal domains of the HSP70 or HSP60 families. Further examples of immunological fusion partners are provided in EP 804 156.

Polypeptides having at least 50%, for example 60%, 70%, 80%, 90%, 95% or 98% sequence identity to SEQ ID NO:2, SEQ ID NO: 4 or SEQ ID NO:6 may be polypeptides which are amino acid sequence variants, alleles, derivatives or mutants of SEQ ID NO:2, SEQ ID NO: 4 or SEQ ID NO:6 respectively, and are also provided by the present invention. For example such a polypeptide may have an amino acid sequence which differs from that given in SEQ ID NO:2, SEQ ID NO: 4 or SEQ ID NO:6 by one or more of addition, substitution, deletion and insertion of one or more (such as from 1 to 20, for example 2, 3, 4, or 5 to 10) amino acids.

The percentage identity of polypeptide sequences can be calculated using commercially available algorithms which compare a reference sequence (e.g. SEQ ID NO:2, SEQ ID NO: 4 or SEQ ID NO:6 of the present invention) with a query sequence. Further details of assessing identity are described below.

Where a query sequence is determined to have an identity to that of SEQ ID NO:2, SEQ ID NO: 4 or SEQ ID NO:6 of at least 50% and preferably at least 60%, 70%, 80%, 90%, 95% or 98% said sequence being that of a polypeptide retaining NCAM-180 protein activity, such a sequence forms part of the present invention.

A polypeptide according to the present invention may be isolated and/or purified (e.g. using an antibody) for instance after production by expression from encoding nucleic acid. The isolated and/or purified polypeptide may be used in formulation of a composition, which may include at least one additional component, for example a pharmaceutical composition including a pharmaceutically acceptable excipient, vehicle or carrier.

A polypeptide according to the present invention may be used as an immunogen or otherwise in obtaining specific antibodies. Antibodies are useful in purification and other manipulation of polypeptides, diagnostic screening and therapeutic contexts.

A polypeptide of the invention may be labelled with a revealing label. The revealing label may be any suitable label which allows the polypeptide to be detected. Suitable labels include radioisotopes, e.g. $^{125}$I, fluorochromes, enzymes, antibodies, polynucleotides and linkers such as biotin. Labelled polypeptides of the invention may be used in diagnostic procedures such as immunoassays in order to determine the amount of a polypeptide of the invention in a sample. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container along with suitable reagents, controls, instructions and the like.

Such polypeptides and kits may be used in methods of detection of antibodies to such polypeptides present in a sample or active portions or fragments thereof by immunoassay.

Immunoassay methods are well known in the art and will generally comprise:
  (a) providing a polypeptide comprising an epitope bindable by an antibody against said protein;
  (b) incubating a biological sample with said polypeptide under conditions which allow for the formation of an antibody-antigen complex; and
  (c) determining whether antibody-antigen complex comprising said polypeptide is formed.

Sequence Identity

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI-BLAST, which may be used with default parameters.

The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4.

Another method for determining the best overall match between a nucleic acid sequence or a portion thereof, and a query sequence is the use of the FASTDB computer program based on the algorithm of Brutlag et al (Comp. App. Biosci., 6; 237-245 (1990)). The program provides a global sequence alignment. The result of said global sequence alignment is in percent identity. Suitable parameters used in a FASTDB search of a DNA sequence to calculate percent identity are: Matrix=Unitary, k-tuple=4, Mismatch penalty=1, Joining Penalty=30, Randomization Group Length=0, Cutoff Score=1, Gap Penalty=5, Gap Size Penalty=0.05, and Window Size=500 or query sequence length in nucleotide bases, whichever is shorter. Suitable parameters to calculate percent identity and similarity of an amino acid alignment are: Matrix=PAM 150, k-tuple=2, Mismatch Penalty=1, Joining Penalty=20, Randomization Group Length=0, Cutoff Score=1, Gap Penalty=5, Gap Size Penalty=0.05, and Window Size=500 or query sequence length in nucleotide bases, whichever is shorter.

Vectors

Nucleic acid sequences of the present invention may be incorporated into vectors, particularly expression vectors. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, phagemid or baculoviral, cosmids, YACs, BACs, or PACs as appropriate. Vectors include gene therapy vectors, for example vectors based on adenovirus, adeno-associated virus, retrovirus (such as HIV or MLV) or alpha virus vectors.

The vectors may be provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in methods of gene therapy. Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

The vectors may include other sequences such as promoters or enhancers to drive the expression of the inserted nucleic acid, nucleic acid sequences so that the polypeptide is produced as a fusion and/or nucleic acid encoding secretion signals so that the polypeptide produced in the host cell is secreted from the cell.

Vectors for production of polypeptides of the invention of for use in gene therapy include vectors which carry a minigene sequence of the invention.

For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides. Polypeptides may also be expressed in vitro systems, such as reticulocyte lysate.

A further embodiment of the invention provides host cells transformed or transfected with the vectors for the replication and expression of polynucleotides of the invention. The cells will be chosen to be compatible with the said vector and may for example be bacterial, yeast, insect or mammalian. The host cells may be cultured under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers Polynucleotides according to the invention may also be inserted into the vectors described above in an antisense orientation in order to provide for the production of antisense RNA or ribozymes.

Diagnostic Methods

In a preferred embodiment, the invention involves methods to assess quantitative and qualitative aspects of NCAM-180 gene expression. In one example the increased expression of an NCAM-180 gene or gene product as provided by the present invention are indicative of the presence of cancer in a subject or the risk of metastasis of a cancer in said subject. Techniques well known in the art, e.g., quantitative or semi-quantitative RT PCR or Northern blot, can be used to measure expression levels of NCAM-180.

The measurement of NCAM-180 gene expression levels may include measuring naturally occurring NCAM-180 transcripts and variants thereof as well as non-naturally occurring variants thereof. The diagnosis and/or prognosis of cancer in a subject, however is preferably directed to detecting a naturally occurring NCAM-180 gene product or variant thereof. Thus, the invention relates to methods of diagnosing and/or predicting cancer in a subject by measuring the expression of an NCAM-180 gene in a subject. For example an increased level of mRNA encoded by an NCAM-180 nucleic acid sequence (e.g., SEQ ID NO: 1, 3 or 5).

Diagnostic methods for the detection of NCAM-180 nucleic acid molecules, in patient samples or other appropriate cell sources, may involve the amplification of specific gene sequences, e.g., by PCR (See Mullis, K. B., 1987, U.S. Pat. No. 4,683,202), followed by the analysis of the amplified molecules using techniques well known to those of skill in the art, such as, for example, those listed above. Utilizing analysis techniques such as these, amplified sequences can be compared to the levels in control samples.

The diagnosis and/or prognosis of cancer pertain to the detection of naturally occurring NCAM-180 polypeptides in a subject. Detection of an NCAM-180 polypeptide may be by any method known in the art.

The tissue or cell type to be analyzed generally includes those which are known, or suspected, to express the NCAM-180 gene, such as, for example, cancer cells including lung cancer cells, ovarian cancer cells, skin cancer cells, lymphoid cancer cells, and metastatic forms thereof. The protein isolation methods employed herein may, for example, be such as those described in Harlow and Lane (Harlow, E. and Lane, D., 1988, Antibodies: A Laboratory Manual, Cold Spring Harbor Laboratory Press, Cold Spring Harbor, N.Y.). The isolated cells can be derived from cell culture or from a patient.

Preferred diagnostic methods for the detection of NCAM-180 gene products or conserved variants or peptide fragments thereof, in particular Exon18_MUM, may involve, for example, immunoassays wherein the NCAM-180 gene products or variants thereof, including peptide fragments such as Exon18_MUM are detected by their interaction with selective antibodies. For example, antibodies, or fragments of antibodies, may be used to quantitatively or qualitatively detect the presence of NCAM-180 encoded polypeptides or naturally occurring variants or peptide fragments thereof. The antibodies (or fragments thereof) useful in the present invention may, additionally, be employed histologically, as in immunofluorescence or immunoelectron microscopy, for in situ detection of NCAM-180 gene products or conserved variants or peptide fragments thereof. In situ detection may be accomplished by removing a histological specimen from a subject, such as paraffin embedded sections of tissue, e.g., lung tissue, and applying thereto a labeled antibody of the present invention. The antibody (or fragment) is preferably applied by overlaying the labeled antibody (or fragment) onto a biological sample. Since the NCAM-180 fragment Exon18_MUM appears to be expressed predominantly as an intracellular protein, it may be desirable to introduce the antibody into the cell, for example, by making the cell membrane permeable. Some of the NCAM-180 immunogenic polypeptides may also be expressed on the cell surface, thus cells can be directly labeled by applying antibodies that are specific or selective for the extracellular NCAM-180 polypeptides or fragment thereof.

Through the use of such a procedure, it is possible to determine not only the presence of the NCAM-180 gene product, or naturally occurring variants thereof or peptide fragments, but also its distribution in the examined tissue. Using the methods of the present invention, those of ordinary skill will readily perceive that any of a wide variety of histological methods (such as staining procedures) can be modified in order to achieve such in situ detection.

Immunoassays for NCAM-180 encoded polypeptides or conserved variants or peptide fragments thereof, in particular for Exon18_MUM will typically comprise contacting a sample, such as a biological fluid, tissue or a tissue extract, freshly harvested cells, or lysates of cells which have been incubated in cell culture, in the presence of an antibody that specifically or selectively binds to an NCAM-180 gene product, e.g., a detectably labeled antibody capable of identifying NCAM-180 polypeptides or conserved variants or peptide fragments thereof, and detecting the bound antibody by any of a number of techniques well-known in the art (e.g., Western blot, ELISA, FACS). The biological sample may be brought in contact with and immobilized onto a solid phase support or carrier such as nitrocellulose, or other solid support that is capable of immobilizing cells, cell particles or soluble proteins. The support is washed with suitable buffers followed by treatment with a blocking agent and the labeled antibody that selectively or specifically binds to an NCAM-180 encoded polypeptide. The solid phase support is washed with buffer a second time to remove unbound antibody. The amount of bound label on a solid support may be detected by conventional means. Alternatively, the antibody that selectively or specifically binds to an NCAM-180 encoded polypeptide is immobilized, and the biological sample comprising an By "solid phase support or carrier" is intended any support capable of binding an antigen or an antibody. Well-known supports or carriers include glass, polystyrene, polypropylene, polyethylene, dextran, nylon, nitrocellulose, natural and modified celluloses, polyacrylamides, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The anti-NCAM-180 antibody can be detectably labeled by linking the same to an enzyme and using the labeled antibody in an enzyme immunoassay (EIA) (Voller, A., "The Enzyme Linked Immunosorbent Assay(ELISA)", 1978, Diagnostic Horizons 2: 1, Microbiological Associates Quarterly Publication, Walkersville, Md.); Voller, A. et al., 1978, J. Clin. Pathol. 31: 507-520; Butler, J. E., 1981, Meth. E4Zy7n01. 73: 482; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme that is bound to the antibody will react with an appropriate substrate, preferably a fluoresceinisothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals are attached to an antibody using such metal chelating groups as diethylenetriaminepentacetic acid (DTPA) or ethylenediaminetetraacetic acid (EDTA). Fluorochromes typically used are Fluorescein, Texas Red or other fluorochromes such as the Alexa Fluor series.

The antibody can also be detectably labeled by coupling it to a chemiluminescent compound. The presence of the chemiluminescent-tagged antibody is detected by luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of a chemiluminescent reaction. The presence of a bioluminescent protein is determined by detecting luminescence. Important bioluminescent compounds for purposes of labeling are luciferin, luciferase and aequorin.

In various embodiments, the present invention provides methods for the measurement of NCAM-180 polypeptides, and the uses of such measurements in clinical applications using NCAM-180-specific or NCAM-180-selective antibodies.

The measurement of NCAM-180 polypeptides of the invention is valuable for detecting and/or staging lung cancer and other cancers in a subject, for screening of lung cancer and other cancers in a population, for differential diagnosis of the physiological condition of a subject, and for monitoring the effect of a therapeutic treatment on a subject.

The present invention also provides for detecting, diagnosing, or staging lung cancer and other cancers, or for monitoring the treatment of lung cancer and other cancers by measuring the level of expression of an NCAM-180 polypeptide. In addition to NCAM-180 polypeptides, at least one other marker, such as receptors or differentiation antigens can also be measured. For example, serum markers selected from, for example but not limited to, carcino embryonic antigen (CEA), CA15-3, CA549, CAM26, M29, CA27.29 and MCA can be measured in combination with an NCAM-180 polypeptide to detect, diagnose, stage, or monitor treatment of lung cancer and other cancers. In another embodiment, the prognostic indicator is the observed change in different marker levels relative to one another, rather than the absolute levels of the markers present at any one time. These measurements can also aid in predicting therapeutic outcome and in evaluating and monitoring the overall disease status of a subject.

Vaccination Methods

The invention also relates to the use of a vaccine based on NCAM-180 as a tumor-associated antigen (TAA), its epitope, mimotope, specific or anti-idiotypic antibody, for preparing a medicament, as well as to a kit for the prophylactic and/or therapeutic active immunization against cancer. Tumor-associated antigens (TAA) often are the basis for the development of immunotherapeutic agents for the prophylaxis and/or treatment of cancer. TAA are structures that enable a differentiation relative to non-malignant tissue and thus are viewed as targets for the diagnostic and therapeutic applications of specific antibodies. TAA are typically expressed on the plasma membrane of tumor cells but can also be intracellular proteins including nuclear, cytosolic and transmembrane proteins.

Direct therapeutic applications of antibodies against TAA are based on passive immunotherapies, i.e., a specific antibody is systemically (or locally, e.g. into a vein leading into the tissue) administered to cancer patients in a suitable amount and has only a therapeutic action as long as its concentration in the organism is high enough for this. The biological half-life of such agents depends on their structures and ranges from a few hours to several days. Therefore, it is necessary to provide repeated applications. When using xenogenic antibodies (e.g. murine monoclonal antibodies, MAB), this, however, will lead to undesired immune reactions which can neutralize a possible therapeutic activity and may cause dangerous side effects (anaphylactic reactions). Therefore, such immune therapeutic agents can be administered for a limited time only.

A different approach for the immunotherapy of cancer is based on the selective activation of the immune system of cancer patients to fight malignant cells. This is attempted by the most varying forms of cancer vaccines. Among them are vaccinations with irradiated or otherwise inactivated (not proliferative) autologous or allogenic tumor cells or mixtures of autologous, chemically or molecular-biologically modified autologous or allogenic tumor cells, isolated TAAs or TAAs prepared with the help of chemical or molecular-biological methods, peptides derived therefrom, more recently also vaccinations with DNA which codes for TAA or structures derived therefrom, etc. An alternative method is based on the use of anti-idiotypic antibodies for vaccinating against cancer. Suitable anti-idiotypic antibodies may mimic a TAA immunologically. As foreign proteins (e.g. murine antibodies, goat antibodies etc.) they induce a strong immune response in humans after a vaccination-in contrast to the human tumor antigens proper which, being self-structures, often are of only little immunogenicity. Therefore, anti-idiotypic antibodies can be used as an immunogenic substitute of a tumor antigen for vaccination purposes.

In contrast to the passive immunotherapies using anti-tumor antibodies, in principle very small amounts of a suitable vaccine might suffice for the active specific cancer immunotherapy so as to induce an immunity for months or even years which, when it becomes weaker, can be boosted by booster vaccinations. Moreover, in an active immunization both a humoral and also a cellular immunity can be induced whose interaction may yield an effective protective action.

Summing up, so far the use of antibodies or their derivatives in the cancer immunotherapy has essentially been based on two principles:

Passive therapy with antibodies or their derivatives which are directed against TAA. In this instance, tumor cells are relatively specifically destroyed (Immunology Today (2000), 21: 403-410; Curr. Opin. Immunol. (1997), 9: 717).

Active immunization (vaccination) with cells, TAA, or antibodies, respectively, or their derivatives, which are directed against the idiotype of antibodies having a specificity against TAA. The active vaccination triggers an immune response against TAA. This immune response thus is also directed against the corresponding tumor cells (Ann. Med. (1999), 31: 66; Immunobiol. (1999), 201:1).

The present invention now has as its object to provide a vaccine based on a NCAM-180 as tumor-associated antigen (TAA), its epitope, mimotope, specific or anti-idiotypic antibody is used for preparing a medicament which is employed for the prophylactic and/or therapeutic active immunization against cancer, optionally in combination with chemotherapy.

The TAA preferably is selected from the group of the peptides or proteins as described herein, in particular NCAM-180 or Exon18_MUM as described herein before. In an even further embodiment the TAA is selected from the group consisting of:

an isolated protein consisting essentially of SEQ ID NO:2, SEQ ID NO: 4, SEQ ID NO: 6; or to a fragment said isolated proteins, wherein said fragment is capable of inducing a humoral or a cellular immune response in a mammal and comprises an epitope selected from;

```
PAASNLSSSVLAN (AA 101-113 of SEQ ID NO: 2),

VLSPSAPAGVG (AA 117-127 of SEQ ID NO: 2),

LAAAAAPATEAPQ (AA 153-165 of SEQ ID NO: 2),

KGPDPEPTQPGA (AA 174-185 of SEQ ID NO: 2)
and

DFKMDEGNFK (AA 216-225 of SEQ ID NO: 2).
```

The TAAs used in the vaccine according to the invention preferably induce a functional immune response directed against tumor cells. In doing so, not only tumor cells during their cell division, but also in the dormant state (e.g. tumor-stem cells as was recently shown), are to be attacked for an effective treatment of the "minimal residual disease", or the reduction of the metastasizing potential. According to the invention, preferably epithelial cancers, such as breast cancer, cancer of the stomach and intestines, of the prostate, pancreas, ovaries and the lung, e.g. SCLC ("small cell lung cancer") and NSCLC ("non small cell lung cancer") will be or can be treated.

In a particular embodiment, according to the invention at least two equal or different epitopes of the NCAM-180 TAA, are provided, or imitated, respectively, in the vaccine. Thus, by the active immunization, a plurality of antibodies with specificity for the same molecule, yet for different NCAM-180 binding sites, can be generated.

The vaccine can also comprise a glycosilated antibody, particularly if the glycosilation itself can also imitate an epitope of a carbohydrate epitope of the TAA. This antibody may particularly well imitate cellular tumor antigens, and accordingly, it causes the desired immune response for the inhibition of epithelial tumor cells.

According to the invention, the vaccine may be used for active immunization, and therefore it is administered in small amounts only. Thus, no particular side effects are expected, particularly no fever and no increase in the glucose level, even if the immunogenic active substance used according to the invention is derived from a non-human species, such as a murine antibody. However, it is assumed that a recombinant, chimeric as well as a humanized or human active substance combined with murine and human components will be particularly suitable for an administration to humans. On the other hand, a murine portion in the active substance by being foreign may additionally provoke the immune response in humans.

Although, naturally, the vaccine used according to the invention may contain an active substance derived from a native antibody, which possibly has been isolated from an organism or patient, often an antibody-derivative is used which preferably is selected from the group of antibody fragments, conjugates or homologues, but also complexes and adsorbates. In any case, it is preferred for the antibody derivative to contain at least parts of the Fab fragment, preferably together with at least parts of the F(ab')2-fragment, and/or parts of the hinge-region and/or of the Fc-part of a lambda or kappa antibody. Furthermore, also a single-chain antibody derivative, such as a so-called single chain antibody may be used in a vaccine as defined by the invention. Preferably, an antibody of the type of an immunoglobulin, e.g. an IgG, IgM or IgA, is used. Particularly preferably an IgG2a-antibody is used, since IgG2a antibodies exhibit a particularly good complement activation, resulting in an increased immunogenicity of the vaccine. This, moreover, has the advantage that the content of antibody in the vaccine can be further reduced.

According to the invention, preferably also a vaccine is used which comprises an antibody or an antibody derivative directed against a tumor-associated antigen, i.e. an ab1. The specificity of the antibody preferably is chosen from among the above-mentioned groups of the TAAs, in particular selected from the group of NCAM-180 or Exon18_MUM.

A particularly preferably used vaccine contains an antibody which specifically binds an antibody. The tumor vaccine thus contains in particular anti-idiotypic antibodies, i.e. ab2, for an active immunization. Antiidotypic antibodies used according to the invention preferably again recognize the idiotype of an antibody which is directed against the TAA. In this manner, already an epitope of a TAA on the paratope of the anti-idiotypic antibody is formed as a mimic for the TAA. Here, too, the preferred selection is made from the above-indicated groups of the TAAs.

The vaccine used according to the invention advantageously is provided in a suitable formulation. Preferred are such formulations with a pharmaceutically acceptable carrier. This comprises, e.g., auxiliary substances, buffers, salts, preservatives. The vaccine may, e.g., be used for the prophylaxis and therapy of cancer-associated conditions, such as metastasis formation and minimal residual disease of cancer patients. In this instance, antigen-presenting cells are specifically modulated in vivo or also ex vivo so as to specifically generate the immune response against the TAA and the tumor cells.

Accordingly, in case of an active immunization, it is also an object of the present invention to provide a vaccine formulation that contains the immunogenic active substance in most cases only at low concentrations, such as in an immunogenic amount ranging from 0.01 [mu]g to 10 mg. Depending on the nature of the TAA, its epitope, mimotope, specific or anti-idiotypic antibody, depending on the use of species-foreign sequences or derivatization, but also depending on the auxiliary agents or adjuvants, respectively, used, the suitable immunogenic dose will be chosen, e.g. in the range of from 0.01 [mu]g to 750 [mu]g, preferably 100 [mu]g to 500 [mu]g. A depot vaccine which is to be delivered to the organism over an extended period of time may, however, also contain much higher antibody amounts, such as from at least 1 mg to up to more than 10 mg. The concentration will depend on the administered amount of the liquid or suspended vaccine. A vaccine usually is provided in ready-to-use syringes having a volume of from 0.01 to 1 ml, preferably 0.1 to 0.75 ml, of the concentrated solution, or suspension, respectively.

For the passive immunization as described hereinbefore, the present invention further provides a vaccine formulation comprising the TAA specific antibodies in range of from 1 mg to 10 gr, preferably from 10 mg to 1 gr.

The vaccine used according to the invention preferably presents the immunogen or antibody in a pharmaceutically acceptable carrier which is suitable for a subcutaneous, intramuscular or also intradermal or transdermal administration. A further type of administering is via the mucosal pathway, such as a vaccination by nasal or peroral administration. If solids are employed as auxiliary agents for the vaccine formulation, e.g. an adsorbate or a suspended mixture of the antibody with the auxiliary agent is administered. In special embodiments, the vaccine is administered as a solution, or liquid vaccine, respectively, in an aqueous solvent.

Preferably, one or more vaccine units of the tumor vaccine are already provided in suitable ready-to-use syringes. As an antibody is relatively stable as compared to the TAA, vaccines based on antibodies or their derivatives have the essential advantage that they can be put on the market as a storage-stable solution or suspension in a ready-to-use form. However, a content of preserving agents, such as thimerosal or other preserving agents with an improved tolerance is not necessary, may, however, be provided in the formulation for a longer durability at storage temperatures of from refrigerator temperatures up to room temperature. The vaccine used according to the invention may, however, also be provided in frozen or lyophilized form which may be thawed, or reconstituted, respectively, when needed.

In any case, it has proven suitable to increase the immunogenicity of the active substance used according to the invention by using adjuvants in the vaccine formulation. Vaccine adjuvants suitable therefor preferably are aluminum hydroxide (Alu gel) or -phosphate, also growth factors, lymphokines, cytokines, such as IL-2, IL-12, GM-CSF, gamma interferon or complement factors, such as C3d, furthermore liposome preparations, and also formulations with additional antigens, against which the immune system has already produced a strong immune response, such as tetanus toxoid, bacterial toxins, such as *Pseudomonas* exotoxins and derivatives of Lipid A.

An adjuvant which allows for the medicament to be administered without any side effects is preferred. The term side effects encompasses, e.g., an increased glucose level or fever; local reddenings at the site of administration or slight swellings are not considered to be special side effects but indicate that an immune reaction is going on.

To formulate the vaccine, also further known methods for conjugating or denaturing vaccine components may be used so as to further increase the immunogenicity of the active substance. Particular embodiments of the vaccine used according to the invention comprise further vaccination antigens, in particular additional anti-idiotypic antibodies, also mixtures of immunogenic antibodies with various antibodies which are simultaneously administered.

When combined with chemotherapy, the use according to the invention of the vaccine is preferably at the beginning of the chemotherapy. Preferably, chemotherapy is started within 1 to 2 weeks. A vaccination simultaneously with and/or during the chemotherapy is also preferred for practical reasons. The patient is already under clinical treatment, the additional therapeutic measures are easy to carry out. If the immunotherapy is already effected on the first day of the chemotherapy or within the first 2 to 3 days, the immune system can be activated already at an early point of time, even before the organism has been adversely affected by the chemotherapy. Chemotherapy does, in fact, have side effects, such as that of a weakened immune system, which makes the patient increasingly infection-prone. Precisely for this reason it has been surprising that the immunotherapy can successfully be used immediately before and during the chemotherapy. Thus, it could be observed that the immune response after the inoculation with a tumor vaccine could be induced on the first day, several hours prior to the beginning of the chemotherapy, to the same extent as without a chemotherapeutical treatment. In any event, the serum content of immunoglobulins and vaccination antigen-specific antibodies was persistently increased, irrespective of a chemotherapy. There were even signs that the specific immune response was even increased by the chemotherapy.

The vaccine administration regimen according to the invention contains preferably not only the initial vaccination within the scope of the chemotherapy, but also several booster vaccinations at certain time intervals which for practical reasons possibly can be equal to the intervals of the chemotherapy. Also following the chemotherapy, the long-term immunotherapy over months and years very much is a suitable regimen. Both, the initial vaccination and also later booster vaccinations preferably are effected with the same vaccine. The combination with the adjuvant or palliative chemotherapy is preferred. The combination with a monotherapy or polytherapy is possible. For reasons of the different mechanisms of action, the vaccine preferably is combined with the polychemotherapy.

Preferable agents used for the chemotherapy are alkylating pharmaceutical preparations. Thus, e.g., agents containing taxane, anthracyclins or platinum are preferred. All the conventional preparations which are used for various cancer treatments can be combined according to the invention. The chemotherapeutic agents commonly are administered intravenously or perorally. Peroral forms of administration of the chemotherapeutic agents may possibly also be administered with the peroral form of the vaccine according to the invention as a combination preparation.

A vaccination as defined by the present invention may basically be carried out both for a therapeutic and also for a prophylactic treatment. Such a prophylactic vaccination particularly-though not exclusively-aims at persons that have been diagnosed with cancer and which may have small (single dormant cells, small metastasis) metastasis, but is currently free of any signs of the disease. In such a case the vaccine would be a prophylactic vaccine in that it induces an immune response which might be helpful against a future outbreak of cancer.

In a preferred embodiment, the vaccine used according to the invention comprises an NCAM-180 gene product or an antibody against this gene product, or a corresponding anti-idiotypic antibody, respectively. The methods of formulating a vaccine suitable for the inventive method are known:

The NCAM-180 TAA, its derivatives, epitopes and mimics can be obtained from natural or synthetic sources. Also the antibody components can be chemically synthesized and subsequently connected with epitope structures, or synthesized in common. In a chemical synthesis of antibody carrier molecules it is possible to introduce reactive groups at special sites so as to be able both to control the extent of coupling with an epitope as well as the type and location of the binding.

Immunogenic NCAM-180 TAA, its epitopes, mimics or antibodies, may also be prepared as recombinant molecules by genetic engineering methods. By changing the genetically engineered nucleic acids which encode native molecules, e.g. suitable derivatives can be produced. A glycosylation of a recombinant gene product with corresponding tumor-associated glycan structures can also be effected by a production in cells which have been genetically modified such that they will glycosylate proteins accordingly. Such cells may be natural isolates (cell clones), they can be found by an appropriate screening for the desired glycosylation. Yet, also cells may be modified such that they will express the corresponding enzymes required for the desired glycosylation such that particularly the desired glycosylation will be found on the recombinant polypeptide or protein (Glycoconj. J. (1999), 16: 81). However, it is also possible to enzymatically produce, or change, respectively, the glycosylation pattern of proteins (Clin. Chem. Lab. Med. (1998), 36: 373).

According to a particular embodiment of the present invention, the vaccine used according to the invention comprises a nucleic acid molecule as a precursor for the NCAM-180 TAA, wherein the nucleic acid molecule encodes NCAM-180 gene products as defined by the present invention. The DNA vaccine obtained is administered just like tumor vaccines on protein base.

The present invention also relates to a kit which is suitable for the prophylactic and/or therapeutic treatment of cancer-associated conditions. This kit comprises a) a vaccine based on the NCAM-180 tumor-associated antigen, its epitope, mimotope, specific or anti-idiotypic antibody, and optionally b) an agent for chemotherapy.

The selection of the components of the kit according to the invention as well as their combination is carried out as described before. Preferably, the kit further comprises suitable application devices, such as, e.g., syringes, infusion devices, etc. If the vaccine is provided in lyophilized form, the kit will further contain a suitable reconstituting solution which optionally comprises special stabilizers or reconstitution accelerators. The further preferred kit comprises several units of the vaccine used according to the invention, which will be employed for the initial vaccination as well as for one or more, preferably up to three, booster vaccinations.

The number of booster vaccinations may, however, also be higher, and for this, kits containing several vaccination units alone, without a combination with a chemotherapeutic agent, are offered. The frequency optionally will range from 1 to 12 per year, particularly preferred it will range from 4 to 8 per year. The dosage may remain equal or may decrease. Booster vaccinations can be carried out at regular intervals, in principle life-long. Suitable intervals range from about 6 to 24 months and can be determined by checking the titer of the induced CTL response (a booster should be made as soon as the titers of the induced CTL response has markedly dropped).

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

Experiments to investigate the differential expression of NCAM-180 (Exon18_MUM) in various cell lineages. Differential expression of NCAM-180 was evaluated in different cancer cell lines and healthy controls, using art know procedures including;

RNA extraction and cDNA synthesised according to standard procedures; and

PCR amplification to evaluate the expression of Exon18_MUM according to the principle represented in FIG. 1.

Figure 2:
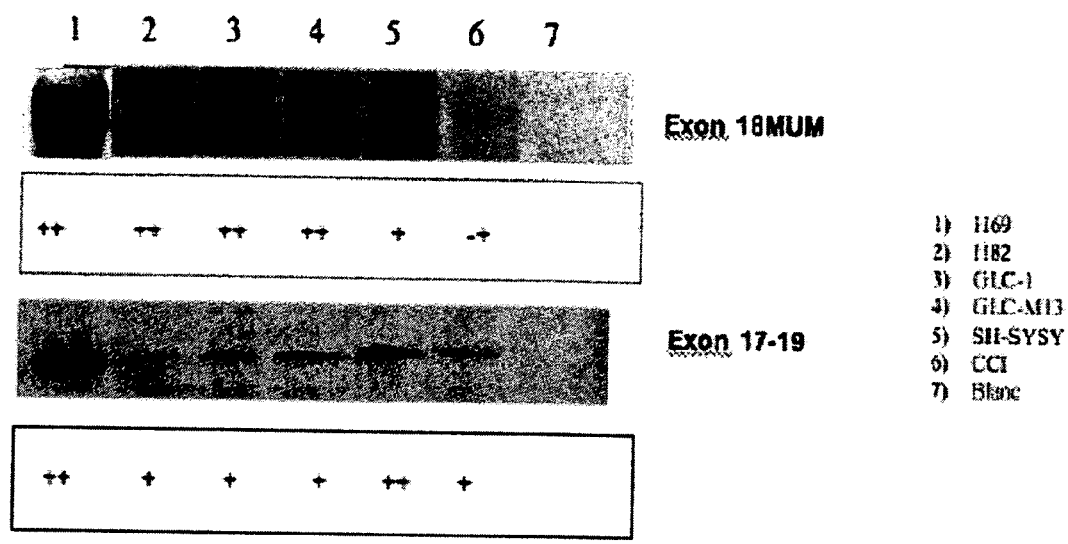
FIG. 2 Overexpression of Exon18_MUM as part of NCAM-180 in cell cultures derived from cell lines from neuroendocrine tumors (SH-SYSY and CCI) and in cell lines derived from small cell lung cancers (H69, H82, GLC-1, GLC1-M13). Cells expressing Exon18_MUM, result in a 604 bp PCR product in the MUM specific PCR. Cells expressing the NCAM-140 splice variant, have a 180 bp product for the exon 17-19 PCR amplification reaction. High expression is marked as (++), medium expression (+), low expression (−+) and no detectable expression (−).

An expression of NCAM Exon18_MUM as part of NCAM-180 was found in cell cultures derived from neuroendocrine tumors (SH-SYSY and CCI) and a clear over-expression more particularly in Small Cell Lung Cancer (SCLC) cell lines (FIG. 2). The results for the other cell lines are summarized in table 1

TABLE 1

Differential expression of Exon18_MUM (NCAM-180) in cancer cell lines and healthy controls.

| Cell line | Cancer type | NCAM17-19 180 bp | NCAM18MUM 604 bp | NCAM - pi 213 bp | NCAM + pi 243 bp |
|---|---|---|---|---|---|
| Lung cancers | | | | | |
| HS-10A | Small cell lung cancer (carcinoma) | + | + | + | + |
| H69 | Small cell lung cancer (Classic) | + | + | + | + |
| H82 | Small cell lung cancer (variant) | + | + | + | + |
| GLC-1 | Small cell lung cancer (variant) | + | + | - | + |
| GLC-1 M13 | Small cell lung cancer (Classic) | + | + | - | - |
| H1437 | Non small cell lung cancer adenocarcinoma | - | - | - | - |
| H520 | Non-small cell lung cancer | + | - | + | + |
| H1299 | Non-small cell lung cancer (from lymph node metastasis) | - | - | - | - |
| H727 | Non-small cell lung cancer | +/- | - | - | + |
| MR65 | Non-small cell lung carcinoma | - | - | - | - |
| A549 | Non-small cell bronchoepithelial carcinoma | - | - | - | - |
| H1792 | Lung adenocarcinoma (from metastatic site pleural effusion) | - | - | - | - |
| H460 | Large cell lung cancer (from metastatic site: pleural effusion) | + | + | + | + |
| H720 | Atypical lung carcinoid | + | - | + | + |

TABLE 1-continued

Differential expression of Exon18_MUM (NCAM-180) in cancer cell lines and healthy controls.

| | | | | | |
|---|---|---|---|---|---|
| Non lung cancers | | | | | |
| PC3 | Prostate adenocarcinoma (from bone metastatis) | - | - | - | - |
| MDA-MB-435s | human breast carcinoma (from metastasis site: pleural effusion) | - | - | - | - |
| JAR | Placenta Choriocarcinoma (often metastatic) | ? | ? | ? | |
| A375 | Skin malignant melanoma | | - | | ? |
| A431 | Skin squamous carcinoma | - | - | - | - |
| SUM 159PT | Anaplastic carcinoma | - | - | - | - |
| HT29 | Epithelial colon adenocarcinoma | - | - | - | - |
| Colo205 | Colon adenocarcinoma | - | - | - | - |
| HCT-116 | Coloncarcinoma | - | - | - | - |
| MCF7 | Breast adenocarcinoma | - | - | - | - |
| MCF7-10A | Nontumorigenic breast epithelial cells (very low ER) | - | - | - | - |
| MDA-MB-239 | Breast carcinoma | - | - | - | - |
| SUM 149PT | Breast cancer intaductal carcinoma | - | - | - | - |
| A2780 | Human ovary carcinoma | - | - | - | - |
| Hela | Cervix cancer | - | - | - | - |
| LnCap | Human prostate carcinoma | - | - | - | - |
| DU145 | Human prostate cancer | - | - | - | - |
| SJSA | Osteosarcoma | ? | + | ? | - |
| Leukemia | | | | | |
| HL60 | Promyelocytic leukemia | - | - | - | - |
| Jurkat | T cell lymphoma | - | - | - | - |
| Molt-4 | Human acute lymphoblastic leukemia | - | - | - | - |
| K562 | Lymphoblast chronic myeloid leukemia | - | - | - | - |
| Neuronal/neuroendocrine | | | | | |
| SH-SYSY | Human neuroblastoma | ? | + | - | ? |
| CCI | Astrocytoma | + | +/- | - | ? |
| U87MG | Brain glioblastoma-astrocytoma | + | - | + | + |
| CM | Insulinoom | - | - | + | + |
| Bon-1 | human enocrine pancreatic tumor cell line | +/- | - | - | + |
| QGP | human pancreatic islet culture | + | - | + | ? |
| Peripheral blood mononuclear cells | | | | | |
| PBMC_1 | Peripheral blood mononuclear cells of healthy control | + | - | + | + |
| PBMC_2 | Peripheral blood mononuclear cells of healthy control | + | - | + | + |
| PBMC_3 | Peripheral blood mononuclear cells of healthy control | + | - | + | + |
| PBMC_4 | Peripheral blood mononuclear cells of healthy control | + | - | - | + |
| PBMC_5 | Peripheral blood mononuclear cells of healthy control | + | - | + | - |
| PBMC_6 | Peripheral blood mononuclear cells of healthy control | + | - | + | + |
| PBMC_7 | Peripheral blood mononuclear cells of healthy control | + | - | - | ? |
| PBMC_8 | Peripheral blood mononuclear cells of healthy control | + | - | - | + |
| PBMC_9 | Peripheral blood mononuclear cells of healthy control | + | - | + | + |
| PBMC_10 | Peripheral blood mononuclear cells of healthy control | + | - | + | + |
| NHK-10 | normal human keratinocytes | - | - | +/- | + |
| CH-ME-3 | human foetal microglial cell | - | - | - | - |

Code: high expression (++), normal expression (+), low expression (+/−), No expression (−).

Cloning and Purification of NCAM Exon18_MUM
A. NCAM Exon18_MUM Cloning

PCR primers were designed. The nucleotide sequence of the complete Exon18_MUM (816 nt) (SEQ ID No. 1) and the nucleotide sequence of a truncated form of the Exon18_MUM (369 nt) (SEQ ID No. 5) were picked up from cDNA of H69 cells. These cells were shown to overexpress the Exon18_MUM. Both the forward and the reverse primer contained restriction sites for sub-cloning into the pRSET (protein production) and the pCI (DNA immunization) vector.

NCAM Exon18_MUM encoding DNA, both full-length and truncated Exon18_MUM, were successfully cloned into:
pRSET (Invitrogen) a construct used for protein production, yielding His-tagged recombinant proteins in *E. coli* with the following protein sequence (SEQ ID No. 2); (the truncated version is shown in italic—SEQ ID No. 6)

```
  1 lpadttatve dmlpsvttvt tnsdtitetf ataqnsptse ttltssiap 51 patatpdsns vpagqatpsk gpsasapspa pasapkvapl vdlsdtptst 101 paasnlsssv lanqgavlsp sapagvgeas kappaskptp apvptptgaa 151 splaaaaapa teapqakqea pstkgpdpep tqpgaakspa eaatalaspk 201 seaasvsttn psqgedfkmd egnfktpdid lakdvfaalg spapaagasg 251 qapelapsta dssvspapak t
``` pCI (Promega) a construct used for DNA immunization.

B. NCAM Exon18_MUM Protein Production and Purification

Figure 3:
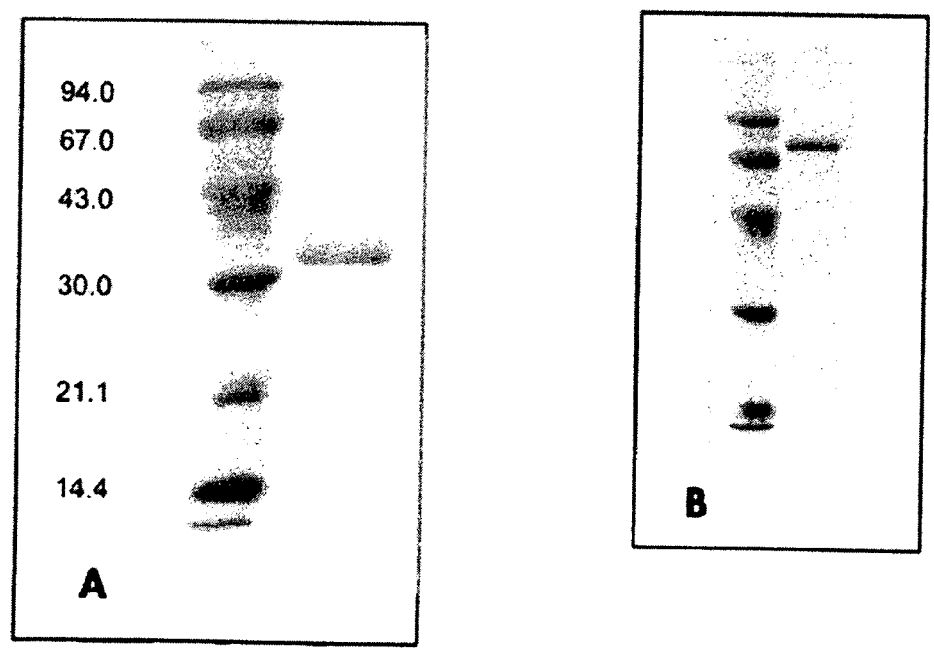
FIG. 3: Purified truncated (panel A) and full-length (panel B) His-NCAM-Exon18_MUM protein produced in E Coli and purified on Ni-chelate columns.

Bacteria were transformed with expression constructs (pRSET, Invitrogen) encoding the Exon18_MUM protein. We used a pRSET construct encoding the truncated NCAM Exon18_MUM protein (marked in italic in the NCAM Exon18_MUM protein sequence above) and a pRSET construct encoding the full length NCAM Exon18_MUM protein sequence. Transformation was performed according to the manufacturer's instructions. Both forms of the protein were expressed as His-tagged proteins and purification was performed on Ni-chelate columns according to standard procedures. His-tagged proteins were eluted from the columns using 300 mM imidazole, and eluted protein solutions were subsequently re-naturated using a standard dialysis against PBS. Purity of the NCAM Exon18_MUM protein products is shown in FIGS. 3 A and B.

Experiments to Validate the Immunogenic Potential of NCAM-180 and NCAM-180 Gene Products as a Candidate Antigen C. Immunizations and Immune Response Measurements C1. NCAM Exon18_MUM Immunization Induces Cellular Immune Responses Based on differential expression PCR, the NCAM Exon18_MUM splice variant was identified as a potential target for lung cancer immunotherapy. As described above, for this novel antigen both DNA and recombinant protein was prepared. Using the above procedure, truncated MUM protein was produced in *E. coli*, purified and subsequently used for immunization of Balb/c mice.

C1.1 Immunization with Exon18_MUM Protein and/or Exon18_MUM DNA and In Vitro Re-Stimulation with an Overlapping 9-Mer Peptide Pool.

In a first type of experiment, some mice were primed, hereinafter also referred to as immunized, with truncated Exon18_MUM protein in PBS, either with or without an adjuvant such as Abisco-100, and some were immunized with Exon18_MUM encoding DNA. In addition immunization with Exon18_MUM protein was combined with Exon18_MUM DNA immunization. At day 21, these different groups were boosted as shown below:

Remark:
Exon18_MUM protein is represented in the table as MUM protein.
Exon18_MUM DNA is represented in the table as MUM DNA
The Adjuvant used is Abisco-100

|   |   |       |         | Immunization t = 0 | Boost t = 21 days |
|---|---|-------|---------|--------------------|-------------------|
| 1 | 4 | BALB/c | females | PBS | PBS |
| 2 | 4 | BALB/c | females | PCI empty vector | PCI empty vector |

-continued

|   |   |       |         | Immunization t = 0 | Boost t = 21 days |
|---|---|-------|---------|--------------------|-------------------|
| 3 | 4 | BALB/c | females | Abisco adjuvant | Abisco adjuvant |
| 4 | 4 | BALB/c | females | MUM protein in Abisco | MUM protein in Abisco |
| 5 | 4 | BALB/c | females | MUM protein w/o adjuvant | MUM protein w/o adjuvant |
| 6 | 4 | BALB/c | females | MUM DNA | MUM DNA |
| 7 | 4 | BALB/c | females | MUM DNA | MUM protein in Abisco |

For protein immunization we used:
10 µg recombinant Exon18_MUM protein in PBS, optionally formulated with 12 µg Absico-100.

For DNA immunization we used:
2×50 µg Exon18_MUM DNA (in pCI-vector) (50 µg into the M. tibialis anterior of each of the two hind legs)

Balb/c mice (n=4 in each group) were immunized on day 0 and boosted on day 21. Thirty days after the first immunization, mouse spleens were isolated, spleen cell suspensions prepared and seeded at a density of $1.5 \cdot 10^6$ cells/well. In vitro re-stimulation was performed for 4 h at 37° C. (5% $CO_2$). Re-stimulation was performed with a pool of overlapping 9-mer peptides covering the full-length amino acid sequence of the truncated MUM protein. A total of 45 overlapping peptides were used. We calculated the number of intracellular IFN-γ containing cells in $10^5$ CD8 positive cells for all mice immunized, as determined by flowcytometry (FIG. 4 group A-G). Our data show a low number of intracellular IFN-γ containing CD8 positive T-cells representing a limited CTL response in the Exon18_MUM protein immunized and boosted animals (FIG. 4 group D). Mice immunized with Exon18_MUM protein in Abisco-100 adjuvant apparently did not induce a CTL response at all (FIG. 4 group C). For the Exon18_MUM DNA immunized mice we found that intramuscular injection of the truncated Exon18_MUM encoding DNA clearly induced a MUM specific cytotoxic T-cell response (FIG. 4 group F and G), when compared to the pCI vector alone immunized mice, performed as control immunization. We found 727 intracellular IFN-γ containing cells on a total of 10⁵ CD8 positive T-cells (0.7%). Our data even suggest a slight increase in the number of intracellular IFN-γ containing CD8 positive T-cells for mice immunized with Exon18_MUM DNA and boosted with Exon18_MUM protein with Abisco-100 (887 intracellular IFN-γ containing cells on 10⁵ CD8 positive T-cells, 0.9%). For all spleens as a negative control, an in vitro re-stimulation with an irrelevant peptide pool (IPP) was performed. Here, as a control a peptide pool covering an NCAM region that differs from the Exon18_MUM sequence, such as for example the NCAM exon 7pi8 region of the NCAM protein. In the present example the IPP consisted of 17 overlapping peptides (9-mers, 5 amino acids overlap) covering a 76 amino acid sequence the NCAM exon 7pi8 region of the NCAM protein.

For neither the recombinant Exon18_MUM protein immunized animals, nor the Exon18_MUM DNA immunized animals, intracellular IFN-γ containing CD8 positive T-cells were found upon re-stimulation with this IPP. Since T-cells from immunized animals cannot be re-stimulated with an IPP, we conclude that the MUM immunization induces MUM specific T-cells.

Based on this experiment we conclude that immunization with recombinant Exon18_MUM protein and Exon18_MUM encoding DNA induces a MUM-specific T-cell response. Exon18_MUM protein immunization only resulted in a limited number of intracellular IFN-γ containing CD8 positive T-cells, whereas immunization with Exon18_MUM encoding DNA induced a significant cellular MUM specific immune response.

Based on the results of these experiments we conclude that:
immunization with Exon18_MUM DNA induces a significant MUM specific cytotoxic T-cell response.
the truncated Exon18_MUM protein alone is immunogenic and induces a MUM specific CTL response, as identified upon re-stimulation with a MUM-related overlapping 9-mer peptide pool.

C1.2 Immunization with Exon18_MUM Protein and/or Exon18_MUM DNA, In Vitro Re-Stimulation with an Overlapping 9-Mer Peptide Pool In the next type of experiment we used for the in vitro re-stimulation individual 9-mer peptides covering the truncated Exon18_MUM protein sequence (9-mer peptides, 5-mer overlap), and not a total 9-mer peptide pool described hereinbefore. In vitro re-stimulation with individual 9-mer peptides was done in order to perform a detailed mapping of CTL epitopes on the Exon18_MUM protein sequence. In each experiment 11 animals were used, 1 negative control mouse, and two groups each of 5 animals that were immunized per group as shown below at day 0 and boosted as shown below at day 21:

Group 1: 1 mice immunized and boosted with 100 µg pCI empty vector
Group 2: 5 mice immunized and boosted with 100 µg MUM DNA
Group 3: 5 mice immunized and boosted with 210 µg NCAM 18MUM protein.

We did 9 experiments, each with 11 animals.

Forty-five animals were immunized with the truncated Exon18_MUM protein, 45 animals with truncated Exon18_MUM DNA and 9 animals with the pCI empty vector.

In each experiment the mice were sacrificed 12-14 days after the boost. Spleens were excised, spleen cell suspensions prepared, seeded in multiwell 96 plates and in vitro re-stimulated with individual NCAM Exon18_MUM 9-mer peptides. In each experiment 5 peptides were tested for in vitro re-stimulation, the experiment was repeated 9 times, 45 peptides were tested in total. This epitope mapping allowed us to localize the best CTL epitopes in the truncated Exon18_MUM protein.

In vitro re-stimulation was performed with a total of 45 overlapping 9-mer MUM peptides covering the AA sequence of the truncated Exon18_MUM protein (table 2).

TABLE 2

| NCAM | Exon18_MUM protein overlapping 9-mer peptide sequences | |
|---|---|---|
| 23 | PLVDLSDTP | (SEQ ID NO: 7) |
| 24 | LSDTPTSTP | (SEQ ID NO: 8) |
| 25 | PTSTPAASN | (SEQ ID NO: 9) |
| 26 | PAASNLSSS | (SEQ ID NO: 10) |
| 27 | NLSSSVLAN | (SEQ ID NO: 11) |
| 28 | SVLANQGAV | (SEQ ID NO: 12) |
| 29 | NQGAVLSPS | (SEQ ID NO: 12) |
| 30 | VLSPSAPAG | (SEQ ID NO: 14) |
| 31 | SAPAGVGEA | (SEQ ID NO: 15) |
| 32 | GVGEASKAP | (SEQ ID NO: 16) |
| 33 | ASKAPPASK | (SEQ ID NO: 17) |
| 34 | PPASKPTPA | (SEQ ID NO: 18) |
| 35 | KPTPAPVPT | (SEQ ID NO: 19) |
| 36 | APVPTPTGA | (SEQ ID NO: 20) |
| 37 | TPTGAASPL | (SEQ ID NO: 21) |
| 38 | AASPLAAAA | (SEQ ID NO: 22) |
| 39 | LAAAAAPAT | (SEQ ID NO: 23) |
| 40 | AAPATEAPQ | (SEQ ID NO: 24) |
| 41 | TEAPQAKQE | (SEQ ID NO: 25) |
| 42 | QAKQEAPST | (SEQ ID NO: 26) |
| 43 | EAPSTKGPD | (SEQ ID NO: 27) |
| 44 | TKGPDPEPT | (SEQ ID NO: 28) |
| 45 | DPEPTQPGA | (SEQ ID NO: 29) |
| 46 | TQPGAAKSP | (SEQ ID NO: 30) |
| 47 | AAKSPAEAA | (SEQ ID NO: 31) |
| 48 | PAEAATALA | (SEQ ID NO: 32) |
| 49 | ATALASPKS | (SEQ ID NO: 33) |
| 50 | ASPKSEAAS | (SEQ ID NO: 34) |
| 51 | SEAASVSTT | (SEQ ID NO: 35) |
| 52 | SVSTTNPSQ | (SEQ ID NO: 36) |
| 53 | TNPSQGEDF | (SEQ ID NO: 37) |
| 54 | QGEDFKMDE | (SEQ ID NO: 38) |

TABLE 2-continued

NCAM Exon18_MUM protein overlapping 9-mer peptide sequences

| 55 | FKMDEGNFK | (SEQ ID NO: 39) |
|----|-----------|-----------------|
| 56 | EGNFKTPDI | (SEQ ID NO: 40) |
| 57 | KTPDTDLAK | (SEQ ID NO: 41) |
| 58 | IDLAKDVFA | (SEQ ID NO: 42) |
| 59 | KDVFAALGS | (SEQ ID NO: 43) |
| 60 | AALGSPAPA | (SEQ ID NO: 44) |
| 61 | SPAPAAGAS | (SEQ ID NO: 45) |
| 62 | AAGASGQAP | (SEQ ID NO: 46) |
| 63 | SGQAPELAP | (SEQ ID NO: 47) |
| 64 | PELAPSTAD | (SEQ ID NO: 48) |
| 65 | PSTADSSVS | (SEQ ID NO: 49) |
| 66 | DSSVSPAPA | (SEQ ID NO: 50) |

For each peptide the re-stimulation was performed in 5-fold. Cells were permeabilised, fixed and stained for intracellular IFN-γ and surface expressed CD8 using fluorescent labeled antibodies. The number of intracellular IFN-γ containing cells per $10^5$ CD8 positive cells was measured by FACS analysis.

Figure 5:
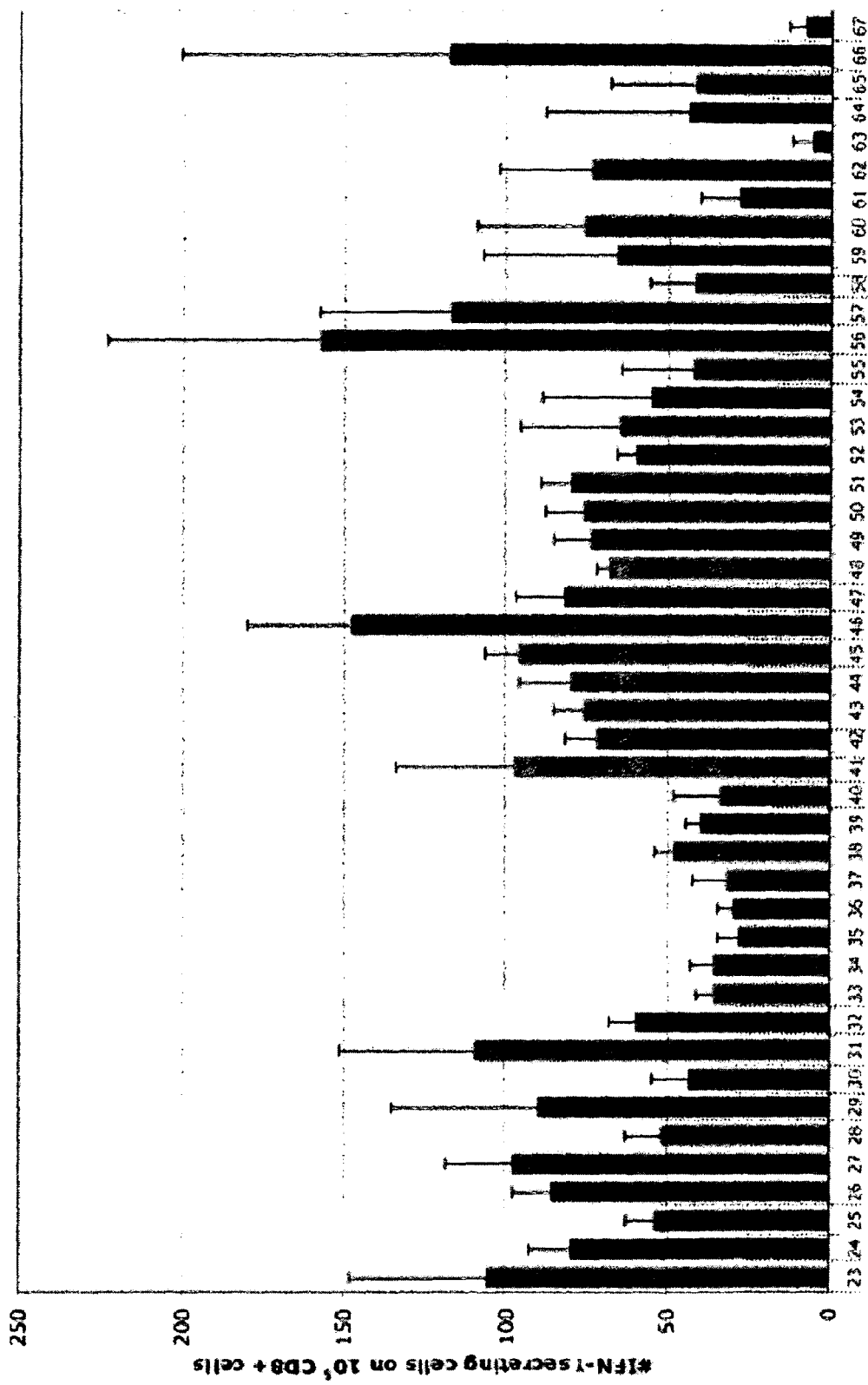
FIG. 5: In Exon18_MUM protein immunized mice cytotoxic T-cell responses were measured. Mouse spleen cells were in vitro re-stimulated with individual 9-mer peptides. The number of intracellular IFN-γ containing CD8 positive T-cells was measured using a FACS based read-out.

Results are show in FIG. 5.

We found that immunization with the truncated Exon18_MUM protein induced MUM specific cytotoxic T-cells as shown by in vitro re-stimulation with peptide 26-27, peptide 30-32, peptide 40-42, peptide 45-47 and peptide 55-58 (FIG. 5). Interestingly, these data show that some specific regions of the truncated MUM recombinant protein are potential CTL epitopes. Moreover these data confirm that the truncated MUM protein is highly immunogenic even without Abisco-100 as was found in the first immunization experiment. In addition, mice were also immunized with NCAM Exon18_MUM plasmid DNA. As shown in FIG. 6A DNA immunization induced a high MUM specific CTL response. In vitro re-stimulation with peptide 25-28, peptide 30-32, peptide 40-44, peptide 45-47, peptide 52-54, peptide 62 and peptide 65 clearly showed that MUM specific cytotoxic T-cells were induced upon immunization of the animals with the Exon18_MUM DNA. When compared with the CTL epitopes from the protein-immunized mice, the peptides 26-27, 30-32, 40-42, 45-47 and peptide 65 were also found in the DNA immunized animals. These data show that against some of the epitopes cytotoxic T-cells are induced in amimals both upon DNA and protein immunization Next, the CTL epitopes as found in Exon18_MUM DNA and Exon18_MUM protein immunization, were compared with the CTL epitopes as predicted by SYPHEITI software. This software was used to predict scores for all the 9-mer peptides for the H2-$D^{d/d}$ haplotype, the MHC haplotype of the Balb/c mice. For all the 9-mer peptides used in the in vitro re-stimulation a score was predicted, these scores are represented in FIG. 6B. Some of the peptides predicted as potential CTL epitopes, which means that these peptides have the potential to re-stimulate in vitro the corresponding in vivo induced cytotoxic T-cell, were indeed confirmed in our experiments in mice. Our data show that in vitro re-stimulation of lymphocytes isolated from Exon18_MUM immunized mice, with any one of peptides 31, 53 and 56, effectively results in re-stimulation of these in vivo primed CD8 positive T-cells in mice.

D. A NCAM Exon18_MUM ELISA

A NCAM Exon18_MUM ELISA was performed as follows. ELISA plates were coated with His-tagged NCAM Exon18_MUM proteins (full length or truncated) and blocked with non-fat dry milk (2%). The serially diluted sera of NCAM Exon18_MUM protein immunized mice are added. MUM specific antibodies induced upon immunization specifically bind to the Exon18_MUM protein on the coated plates. The specificity of the antibodies was confirmed by detecting the binding of the antibodies to a plate coated with His-tagged negative control protein that was also produced in E. coli. Bound antibodies are detected with a horseradish peroxidase conjugated anti-mouse Ig antibody. The conjugated enzyme oxidizes the 3, 3',5,5'-tetramethylbenzidine (TMB) substrate. The reaction is stopped with $H_2SO_4$ and the OD of the oxidized product measured at 450 nm according to standard procedures.

D1. NCAM Exon18_MUM Immunization Induces Humoral Immune Responses

We measured antibody titers in the sera of Balb/c mice immunized with NCAM Exon18_MUM protein and/or Exon18_MUM plasmid DNA. Animals immunized with truncated Exon18_MUM protein both in PBS or in Abisco-100 adjuvant, developed anti-MUM specific serum antibody titers as shown in FIG. 7 group C and D (dark bars). No binding of serum antibodies was shown when ELISA was performed with plates coated with His-tagged negative control protein that was also produced in E. coli (FIG. 7 group C and D (grey bars). These data show that no anti-histidine antibodies or no antibodies against E. coli linked proteins were produced in the serum of the immunized animals. Immunization with plasmid encoding the NCAM Exon18_MUM DNA did not induce serum antibody titers. Only when DNA immunized mice were boosted with formulated NCAM Exon18_MUM protein a clear induction of anti-MUM antibody titers was found (FIG. 7 group F and G). Our data clearly show that immunization of mice with truncated NCAM Exon18_MUM protein induces a significant MUM-specific humoral immune response.

D2. Full-length Exon18_MUM Protein Versus Truncated Exon18_MUM protein based ELISA.

Serum antibody titers of mice immunized with truncated Exon18_MUM protein were measured. The serum was obtained from in total 45 animals immunized with truncated Exon18_MUM protein and 5 mice immunized with empty pCI-vector. The humoral immune responses as detected on ELISA plates coated with full-length Exon18_MUM and truncated Exon18_MUM recombinant protein were compared (FIG. 8).

As shown in FIG. 8, no significant difference was found in the detection of MUM specific antibodies in the sera of immunized animals if coating was done with full-length or truncated Exon18_MUM protein. These data show that when coated with complete Exon18_MUM protein all epitopes as exposed in the truncated Exon18_MUM are still available.

E. Production of Anti-MUM Monoclonal Antibodies

Mice were immunized/boosted with truncated NCAM Exon18_MUM protein according to standard procedures. Spleen cells were fused with NS0 myeloma cells. Fused cells were seeded in HAT selection medium according to standard procedures. Viable clones were selected and the secreted antibody subsequently screened on NCAM Exon18_MUM expressing cells following standard immunocytochemical procedures.

Figure 9:
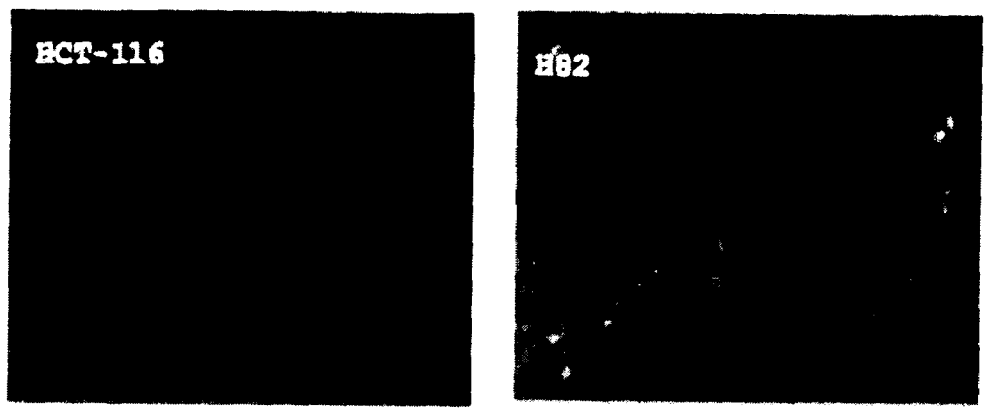
FIG. 9: Fluorescent microscopy of HCT-116 (NCAM-negative), H82 (NCAM Exon18_MUM positive) and H69 (NCAM Exon18_MUM positive) cells stained with monoclonal antibody (IgM) produced by the MUM hybridoma MUMI 21 B2. The Alexa Fluor 488 labeled goat anti-mouse μ-chain secondary antibody (Invitrogen) was used as a secondary antibody for detection of antibody binding.
Figure 10:
FIG. 10: Confocal microscopy image of NCAM Exon18_MUM expressing H69 cells stained with monoclonal antibody (IgM) produced by the MUM hybridoma MUMI 21 B2 in a dilution of 1/2000. The Alexa Fluor 488 labeled goat anti-mouse μ-chain secondary antibody (Invitrogen) was used as a secondary antibody for detection of antibody binding.

Monoclonal antibodies obtained were screened on NCAM Exon18_MUM positive H69 and H82 cells. Finally, one clone was selected, this hybridoma clone produces a monoclonal antibody that shows the specific NCAM-like staining on the NCAM Exon18_MUM expressing cell lines H69 and H82 in immunocytochemical staining. We used the Alexa fluor labeled goat antibodies to mouse IgG as a secondary anti-body and performed the visualization by fluorescent microscopy (FIG. 9). Further selection of clone (MUMI 21 B2) was based on the absence of staining on the NCAM Exon18_MUM negative HCT-116 cells. Moreover, MUMI 21 B2 staining showed a proper localization, at the cell-cell contact regions as shown by confocal imaging (FIG. 10). For these experiments we used antibodies that were enriched using the production in a MiniPerm bioreactor.

In summary, the anti-MUM monoclonal antibody (MUMI 21 B2) that shows an NCAM-like staining on NCAM Exon18_MUM expressing cells, and not on the NCAM Exon18_MUM negative HCT-116 cells.

Experiments to Validate the Immunogenic Potential of NCAM 180 and Exon18_MUM as a Candidate Antigen An animal experiment is performed in which
1) we validate the immunogenic potential of cells expressing NCAM-180 protein or Exon18_MUM protein used as a whole cell vaccine for the treatment of NCAM-180 expressing tumors.

Mice are vaccinated with 200Gy irradiated RVIK (H-2k non-MHC matched-) cells expressing the full size NCAM-180 or the Exon18_MUM, used as a whole cell vaccine.

Tumors expressing the NCAM-180 protein are induced in mice by injection of stably transfected Renca (H-2b MHC matched-) cells expressing the antigen. Protection and immunisation efficiency of the NCAM-180 and Exon18_MUM expressing cells used as a whole cell vaccine is evaluated based on tumor volume and mice survival. CTL and antibody responses are determined respectively in spleen cells (isolated at week 9) and blood samples (taken at the start of the study and after weeks 3, 5 and 7).

2) we validate the immunogenic potential of a DNA construct encoding Exon18_MUM used as a DNA vaccine for the treatment of NCAM-180 expressing tumors.

Mice are vaccinated with a DNA construct encoding Exon18_MUM, used as DNA vaccine. Tumors expressing the NCAM-180 protein are induced in mice using stably transfected Renca (H-2b MHC matched-) cells expressing the antigen. Protection/immunisation efficiency of a DNA vaccination construct encoding the Exon18_MUM is evaluated based on tumor volume and mice survival. CTL and antibody responses are respectively tested in spleen cells (isolated at week 9) and blood samples (taken at the start of the study and after weeks 3, 5 and 7).

3) we validate the immunogenic potential of Exon18_MUM protein, used as a protein vaccine for the treatment of NCAM-180 expressing tumors.

Mice are vaccinated with Exon18_MUM protein, used as a protein vaccine. Tumors expressing the NCAM-180 protein are induced in mice by injection of stably transfected Renca (H-2b MHC matched-) cells expressing the antigen. Protection/immunisation efficiency of Exon18_MUM protein is evaluated based on tumor volume and mice survival. CTL and antibody responses are tested in respectively spleen cells (isolated at week 9) and blood samples (taken at the start of the study and after weeks 3, 5 and 7).

Overview of the vaccinations to evaluate the in vivo effect of NCAM180 and Exon18_MUM expressing cells as a whole cell vaccine.

DNA of Exon18_MUM as a DNA vaccine

Exon18_MUM protein as a protein vaccine

| Balb/c (H-2d) | Vaccination with . . . | Tumor induced with | Expectations | Provides information about |
|---|---|---|---|---|
| Group_a (N = 10) | Saline | Renca + NCAM-180 | Tumor grows, no protection. 0% survival | the inducibility of a Renca tumor with NCAM-180 (Blanco vaccine) |
| Group_b (N = 10) | Renca + NCAM-180 | Renca + NCAM-180 | 100% protection = 100% survival No tumor growth | immunization with whole cell vaccine No information about relevance of NCAM. (positive vaccination control) |
| Group_c (N = 10) | RVIK + NCAM_180 | Renca + NCAM-180 | Protection? Reduced tumor growth? | A whole cell vaccin with NCAM-180 or Exon18_MUM alone as immunogen reduces tumor growth for tumors expressing the NCAM-180. The cellular or humoral immune response. |
| Group_d (N = 10) | RVIK + 18MUM | Renca + NCAM-180 | Protection? Comparison with the immunogenic potential of NCAM-180 + pi. | |
| Group_e (N = 10) | RVIK | Renca + NCAM-180 | No protection | The protective activity of parental RVIK cells |

| Balb/c (H-2d) | Vaccination with... | Tumor induced with | Expectations | Provides information about |
|---|---|---|---|---|
| Group_g (N = 10) | Protein 18MUM | Renca + NCAM-180 | Protection? Reduced tumor volume after immunisation with Exon18_MUM protein. | Exon18_MUM protein based vaccine protects for NCAM-180 expressing tumor growth. |

This model emphasizes that the NCAM 180 protein or Exon18_MUM protein are potential antigens to be used in vaccine development. Furthermore, with this in vivo model the immunogenic potential of Exon18_MUM used as a whole cell vaccine, a DNA vaccine or a protein-based vaccine is compared.

For each group:
immunization is performed with 100 µl ($10^6$ cells (RVIK); 200 Gy irradiated or 50 µg DNA) or 100 µg protein in 30 µl. Vaccination will be done three times with one-week intermediate time.

Tumor is induced with 100 µl ($10^5$ cells (Renca)) expressen NCAM-180. This immunisation is done 1 week after the last vaccination, and is performer only once Tumor growth is measured both horizontal and vertical.

The invention claimed is:
1. A method of diagnosing small cell lung cancer in a subject comprising detecting or measuring an NCAM-180 gene product in a sample derived from said subject, as compared to control levels of NCAM-180 gene product in a non-cancerous sample or a predetermined standard control value for a non-cancerous sample, and diagnosing small cell lung cancer in the subject when a level of the NCAM-180 gene product in the sample from the subject is elevated as compared to a control;
wherein the NCAM-180gene product is:
  (a) an RNA comprising SEQ ID NO:1;
  (b) an RNA comprising SEQ ID NO:3; or
  (c) a protein comprising SEQ ID NO:2, 4, or 6.

2. The method of claim 1, wherein the NCAM-180 gene product is a protein comprising SEQ ID NO:2 or SEQ ID NO:6.

3. The method of claim 1, wherein an antibody that immunospecifically binds to SEQ ID NO:2, SEQ ID NO:4, SEQ ID NO:6 or to a fragment of SEQ ID NO:2 or SEQ ID NO:6, wherein said fragment comprises from 5 to 30 amino acids, is used for detecting or measuring the NCAM-180 gene product.

* * * * *